(12) United States Patent
Ionescu Silverman et al.

(10) Patent No.: US 11,891,626 B2
(45) Date of Patent: Feb. 6, 2024

(54) ISOLATED DISCOGENIC CELLS, METHODS OF USING, AND METHODS OF PREPARING SAME FROM MAMMALIAN TISSUE

(71) Applicant: DiscGenics, Inc., Salt Lake City, UT (US)

(72) Inventors: Lara Ionescu Silverman, Salt Lake City, UT (US); Kevin T. Foley, Germantown, TN (US)

(73) Assignee: DiscGenics, Inc., Salt Lake City, UT (US)

( * ) Notice: Subject to any disclaimer, the term of this patent is extended or adjusted under 35 U.S.C. 154(b) by 0 days.

(21) Appl. No.: 14/212,038

(22) Filed: Mar. 14, 2014

(65) Prior Publication Data
US 2014/0286912 A1    Sep. 25, 2014

Related U.S. Application Data

(60) Provisional application No. 61/794,691, filed on Mar. 15, 2013.

(51) Int. Cl.
| | | |
|---|---|---|
| *C12N 5/0775* | (2010.01) | |
| *C12N 5/077* | (2010.01) | |
| *A61K 35/32* | (2015.01) | |
| *A61F 2/44* | (2006.01) | |

(52) U.S. Cl.
CPC .......... *C12N 5/0662* (2013.01); *A61F 2/442* (2013.01); *A61K 35/32* (2013.01); *C12N 5/0655* (2013.01); *C12N 5/0668* (2013.01); *C12N 2501/11* (2013.01); *C12N 2501/115* (2013.01)

(58) Field of Classification Search
None
See application file for complete search history.

(56) References Cited

U.S. PATENT DOCUMENTS

| | | | |
|---|---|---|---|
| 8,227,246 B2 | 7/2012 | Kukekeov et al. | |
| 2009/0074835 A1* | 3/2009 | Kukekeov | C12N 5/0655 424/423 |
| 2009/0142311 A1 | 6/2009 | Masuda et al. | |
| 2012/0100607 A1* | 4/2012 | Duntsch | C12N 5/0655 435/366 |
| 2012/0171171 A1* | 7/2012 | West | A61K 9/0024 424/93.7 |
| 2012/0219533 A1 | 8/2012 | Josimovic-alasevic et al. | |
| 2013/0078222 A1* | 3/2013 | Sakai | C12N 5/0655 424/93.7 |

FOREIGN PATENT DOCUMENTS

| | | | |
|---|---|---|---|
| CA | 2693767 A1 | 1/2009 | |
| CN | 101802175 A | 8/2010 | |
| CN | 105308176 B | 4/2020 | |
| EP | 2554660 A1 | 2/2013 | |
| JP | 2010532994 A | 10/2010 | |
| JP | WO 2011122601 A1 * | 10/2011 | ........... C12N 5/0655 |
| JP | 2019088302 A | 6/2019 | |
| WO | 03068149 A2 | 8/2003 | |
| WO | WO 2003/068149 | 8/2003 | |
| WO | 2009009020 | 1/2009 | |
| WO | WO 2012/112564 | 8/2012 | |
| WO | 2014143870 A1 | 9/2014 | |

OTHER PUBLICATIONS

Minogue, B.M. et al. 2010. Characterization of the human nucleus pulposus cell phenotype and evaluation of novel marker gene expression to define adult stem cell differentiation. Arthritis & Rheumatism 62(12): 3695-3705. specif. pp. 3695, 3701.*
Gruber, H.E. et al. 2004. Cell-based tissue engineering for the intervertebral disc: in vitro studies of human disc cell gene expression and matrix production within selected cell carriers. The Spine Journal 4: 44-55. specif. pp. 44, 45, 49, 50.*
Hotchin, J.E. 1955. Use of methyl cellulose gel as a substitute for agar in tissue-culturen overlays. Nature 175: 352.*
Pei. M. et al. 2011. A review of decellularized stem cell matrix: a novel cell expansion system for cartilage tissue engineering. European Cells and Materials 22: 333-343. specif. p. 333, 337.*
Diaz-Romero, J. et al. 2008. Immunophenotypic changes of human articular chondrocytes during monolayer culture reflect bona fide dedifferentiation rather than ampflication of progenitor cells. Journal of Cell Physiology 214: 75-83. specif. pp. 78, 79, 80.*
Eng MT. Sakai, D. et al. Intervertebral disc nucleus pulposus stem/progenitor cell, method for culturing same, and application. International Patent Application Publication No. WO 2011/122601(A1). Published: Jul. 8, 2013, pp. 1-26.*
Barlic, A. et al. 2008. Quantiative analysis of gene expression in human articular chondrocytes assigned for autologous implantation. Journal of Orthopaedic Research 26: 847-853. specif. pp. 847, 848, 849, 852.*
Hoshiba, T. 2017. Cultured cell-derived decellularized matrices: a review towards the next decade. Journal of Materials Chemistry B 5: 4322-4331. specif. p. 4325.*
Blanco, J.F. et al. 2010. Isolation and characterization of mesenchymal stromal cells from human degenerated nucleus pulposus. Spine 35(26): 2259-2265. plus Supplemental Data. specif. pp. 2259, 2261, 2262, Supp. data pg.*
Wang, J.Y. et al. 2001. Intervertebral disc cells exhibit differences in gene expression in alginate and monolayer culture. Spine 26(16): 1747-1752. specif. pp. 1747, 1748, 1749, 1750.*

(Continued)

*Primary Examiner* — Michael Barker
*Assistant Examiner* — Sharon M. Papciak
(74) *Attorney, Agent, or Firm* — Dorsey & Whitney LLP

(57) ABSTRACT

The present disclosure relates to discogenic cell populations, methods of deriving, and methods of using them. The presently described discogenic cell populations may be used to restore or regenerate damaged, diseased, or missing intervertebral discs of a subject. The presently described discogenic cell populations can be derived from and administered or implanted into a subject, or may be derived from an unrelated donor.

30 Claims, 18 Drawing Sheets

(14 of 18 Drawing Sheet(s) Filed in Color)

(56) References Cited

OTHER PUBLICATIONS

Murai, K. et al. 2010. Primary immune system responders to nucleus pulposus cells: evidence for immune response in disc herniation. European Cells and Materials 19: 13-21. specif. p. 14.*

Tew, S.R. et al. 2008. Cellular methods in cartilage research: primary human chondrocytes in culture and chondrogenesis in human bone marrow stem cells. Methods 45: 2-9; specif. pp. 2, 3, 6, 7.*

Urban, J.P.G. et al. 2003. Review. Degeneration of the intervertebral disc. Arthritis Research & Therapy 5(3): 120-130; specif. p. 122 (Year: 2003).*

Anderson, D. Greg et al., "Cell-based therapies for disc repair", The Spine Journal. 2005;5:297S-303S.

Blanco, Juan F. et al., "Isolation and characterization of mesenchymal stromal cells from human degenerated nucleus pulposus: comparison with bone marrow mesenchymal stromal cells from the same subjects", Spine. 2010;35(26):2259-65. Epub Jul. 14, 2010.

Chelberg, Mary K. et al., "Identification of heterogeneous cell populations in normal human intervertebral disc", Journal of anatomy. 1995;186(Pt 1):43-53.

Ciapetti, Gabriela et al., "Ex vivo observation of human intervertebral disc tissue and cells isolated from degenerated intervertebral discs", European spine journal : official publication of the European Spine Society, the European Spinal Deformity Society, and the European Section of the Cervical Spine Research Society. 2012;21 (Supple 1):S10-9.

Coric, Domagoj et al., "Prospective study of disc repair with allogeneic chondrocytes", Presented at the 2012 Joint Spine Section Meeting. Journal of Neurosurgery: Sppine. 2012;18(1):85-95.

Davis, Matthew A. et al., "Where the United States Spends its Spine Dollars", Spine. 2012;37(19):1693-701.

Erwin, W. Mark et al., "Intervertebral disc-derived stem cells: implications for regenerative medicine and neural repair", Spine. 2013;38(3):211-6.

Feng, Gang et al., "Multipotential differentiation of human anulus fibrosus cells: an in vitro study", The Journal of bone and joint surgery American volume. 2010;92(3):675-85.

Fujita N et al: "CD24 is expressed specifically in the nucleus pulposus of intervertebral discs", Biochemical and Biophysical Research Communications, Academic Press Inc. Orlando, FL, US, vol. 338, No. 4, Dec. 30, 2005 (Dec. 30, 2005), pp. 1890-1896.

Henriksson, Helena B., et al., Identification of cell proliferation zones, progenitor cells and a potential stem cell niche in the intervertebral disc region: a study in four species:, Spine. 2009;34(21):2278-87.

International Search Report and Written Opinion dated Aug. 25, 2014 for International Application No. PCT/US2014/028026.

Kluba, Torsten et al., "Human anulus fibrosis and nucleus pulposus cells of the intervertebral disc: effect of degeneration and culture system on cell phenotype", Spine. 2005;15(30):2743- 8.

Le Maitre, Christine Lyn et al., "Accelerated cellular senescence in degenerate intervertebral discs: a possible role in the pathogenesis of intervertebral disc degeneration", Arthitis Res Ther. 2007;9(R45).

Liu, Lan-Tao et al., "Characteristics of Stem Cells Derived from the Degenerated Human Intervertebral Disc Cartilage Endplate", PLOS One, vol. 6, No. 10, Jan. 1, 2011 (Jan. 81, 2011), pp. e26285-e26285.

O'Halloran, Damien M. et al., "Tissue-Engineering Approach to Regenerating the Intervertebral Disc", Tissue Engineering Part A 2007;13(8):1927-54.

Orozco, Lluis et al., "Intervertebral disc repair by autologous mesenchymal bone marrow cells: a pilot study", Transplantation. 2011;92(7):822-8. © Lippincott Williams & Wilkins.

Peng, Bao-Gan, "Pathophysiology, diagnosis, and treatment of discogenic low back pain", World Journal of Orthopedics. 2013;18(4):42-52.

Pfirrmann, Christian W. A. et al., "Magnetic resonance classification of lumbar intervertebral disc degeneration", Spine. 2001;26(17):1873-8. Epub Sep. 25, 2001.

Risbud, Makarand V. et al., "Evidence for skeletal progenitor cells in the degenerate human intervertebral disc", Spine. 2007;32(23):2537-44. Epub Nov. 6, 2007.

Risbud, Makarand V. et al., "Notochordal Cells in the Adult Intervertebral Disc: New Perspective on an Old Question", Crit Rev Eukaryot Gene Expr. 2011;21(1):29-41.

Roberts, Sally et al., "Histology and pathology of the human intervertebral disc", The Journal of bone and joint surgery American vol. 2006;88(Suppl 2):10-4.

Sakai, Daisuke et al., "Exhaustion of nucleus pulposus progenitor cells with ageing and degeneration of the intervertebral disc", Nat Commun. 2012;3:1264.

Sakai, Daisuke, "Future perspectives of cell-based therapy for intervertebral disc disease", European spine journal: official publication of the European Spine Society, the European Spinal Deformity Society, and the European Section of the Cervical Spine Research Society. 2008;17 Suppl 4:452-8. Epub Nov. 14, 2008.

Sivan, Sarit Sara et al., "Biochemical composition and turnover of the extracellular matrix of the normal and degenerate intervertebral disc", European spine journal : official publication of the European Spine Society, the European Spinal Deformity Society, and the European Section of the Cervical Spine Research Society. 2013;[Epub ahead of print].

Sive, J I et al., "Expression of chondrocyte markers by cells of normal and degenerate intervertebral discs", Molecular pathology: MP. 2002;55(2):91-7. Epub Apr. 16, 2002.

Stefanakis, Mano et al., "Annulus fissures are mechanically and chemically conducive to the ingrowth of nerves and blood vessels", Spine. 2012;15(37):1883-91.

Yoshikawa, Takafumi et al., "Disc regeneration therapy using marrow mesenchymal cell transplantation: a report of two case studies", Spine. 2010;35(11):E475-80. Epub Apr. 28, 2010.

English Translation of First Chinese Office Action for Chinese Patent Application No. 2014800169785, dated Aug. 7, 2017 (4 pages).

European Examination Report for European Application No. 14722454.7, dated Dec. 8, 2016 (4 pages).

European Examination Report for European Patent Application No. 14722454.7, dated Jan. 19, 2018 (4 pages).

English translation of first Office Action for Japanese Patent Application No. 2016-502688, dated Jan. 23, 2018 (4 pages).

Diaz-Romero, Jose et al., "Immunophenotypic Changes of Human Articular Chondrocytes During Monolayer Cuture Reflect Bona Fide Dedifferentiation Rather than Amplification of Progenitor Cells", J Cell Physiol. Jan. 2008; 214(1):75-83.

Fujita, et al., "CD24 is Expressed Specifically in the Nucleus Pulposis of Intervertebral Discs," Biochemical and Biophysical Research Communications, 2005, pp. 1890-1896, vol. 338.

Gruber, Helen E. et al., "Cell-based tissue engineering for the intervertebral disc: in vitro studies of human disc cell gene expression and matrix production within selected cell carriers", Spine J. Jan.-Feb. 2004; 4(1):44-55.

Liu, Lan-Tao et al., "Characteristics of Stem Cells Derived from the Degenerated Human Intervertebral Disc Cartilage Endplate", PLoS One, Oct. 2011; 6(10): e26285; 14 pages.

Minogue, Ben M. et al., "Characterization of the Human Nucleus Pulposus Cell Phenotype and Evaluation of Novel Marker Gene Expression to Define Adult Stem Cell Differentiation", Arthritis Rheum. Dec. 2010; 62(12): 3695-705.

Minogue, Ben M. et al., "Transcriptional profiling of bovine inteavertebral disc cells: implications for identification of normal and degenerate human intervertebral disc cell phenotypes", Arthritis Res Ther. 2010; 12(1): R22, 20 pages.

Office Action received for Canadian Patent Application No. 2,904,138, dated Feb. 4, 2020, 4 pages.

Office Action received for Korean Patent Application No. 10-2015-7029711, dated Feb. 19, 2020, 18 pages including 9 pages of English translation.

* cited by examiner

FIG. 1A

FACs analysis: Percent of cells positive for given marker

| % Cells Expressing | MSC | Fibro. | Chondr. | AD-DC | AI-DC |
|---|---|---|---|---|---|
| CD73 | 99.5 | 99.7 | 99.9 | 98.8 | 94.2 |
| CD90 | 99.9 | 99.7 | 99.6 | 99.2 | 92.1 |
| CD105 | 99.4 | 99.5 | 95.1 | 91.9 | 32.9 |
| CD166 | 98.6 | 96.1 | 98.9 | 87.0 | 9.4 |
| HLA-ABC | 99.7 | 99.4 | 99.2 | 94.4 | 87.9 |

FIG. 4A  Adipogenic
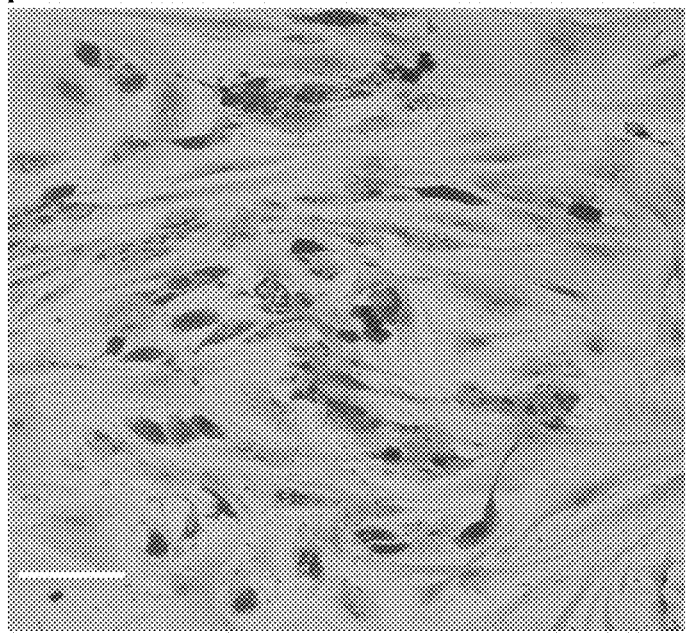
FIG. 4B  Osteogenic
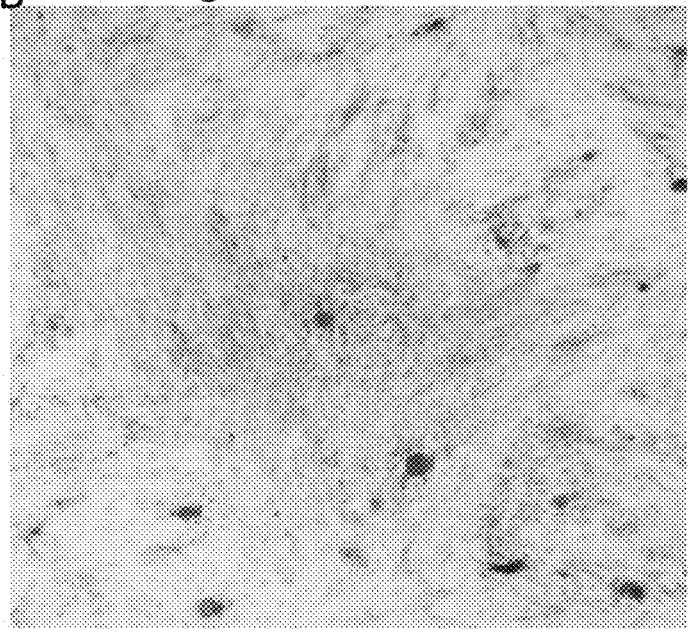

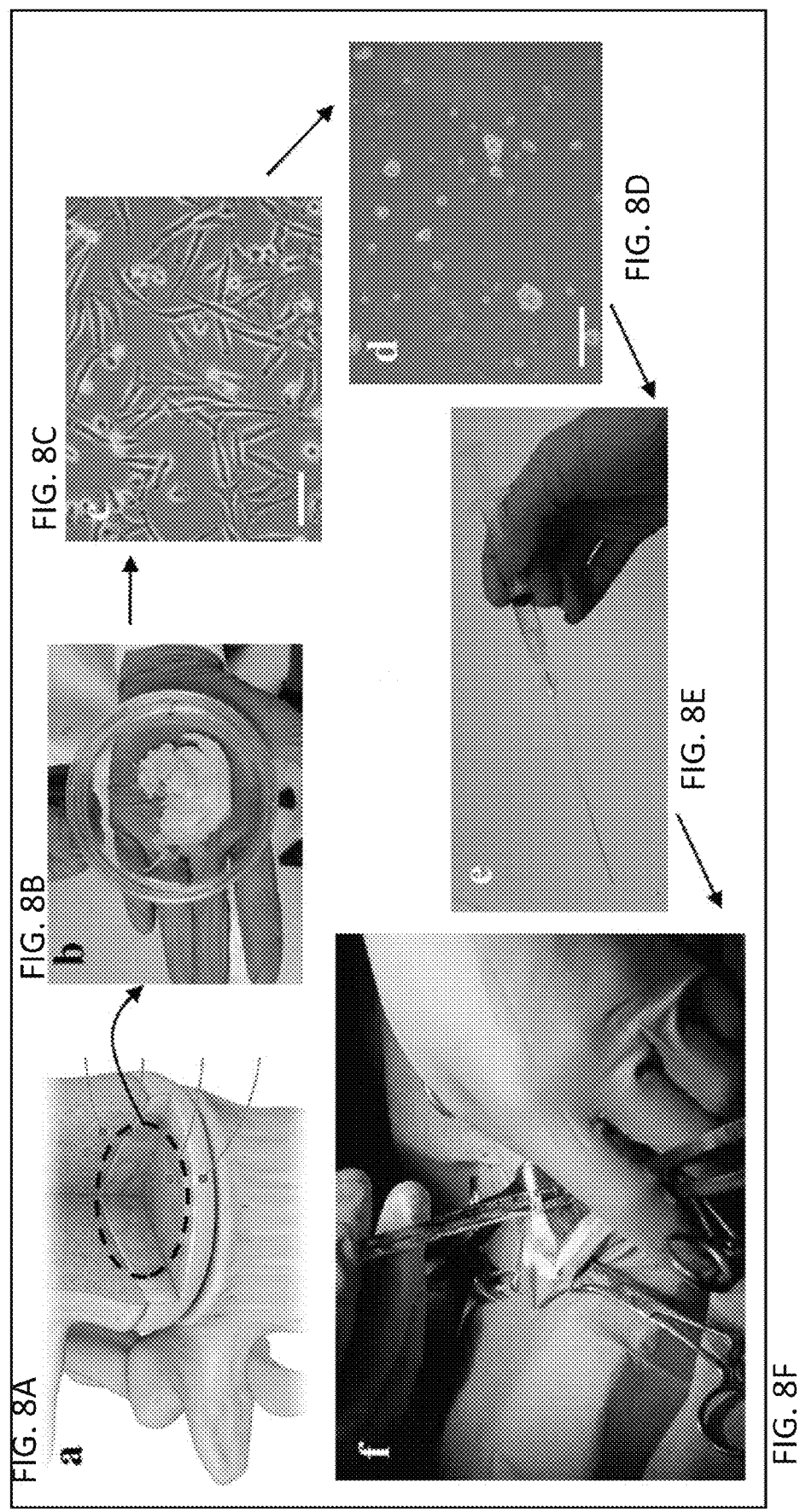

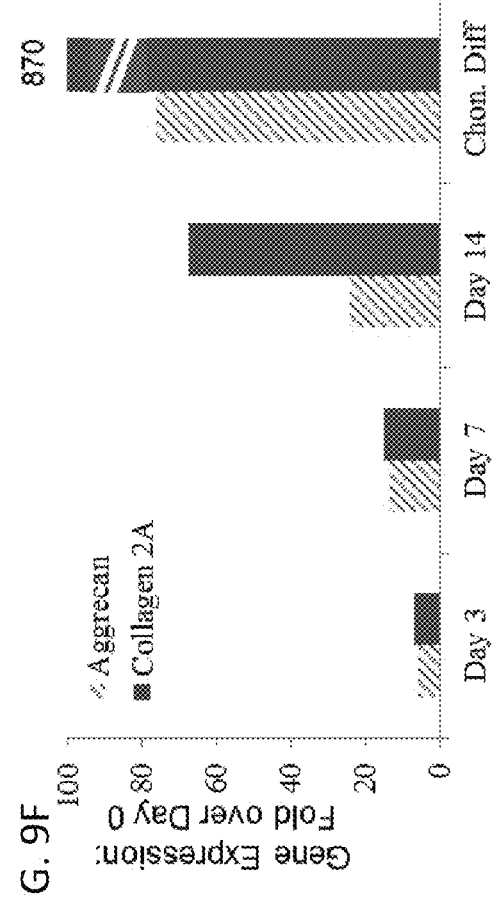
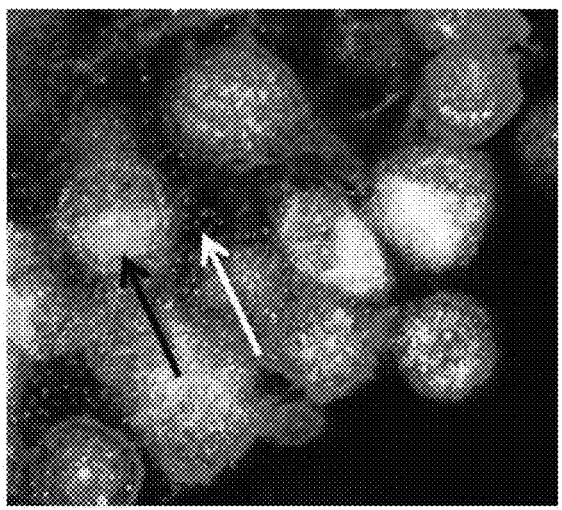
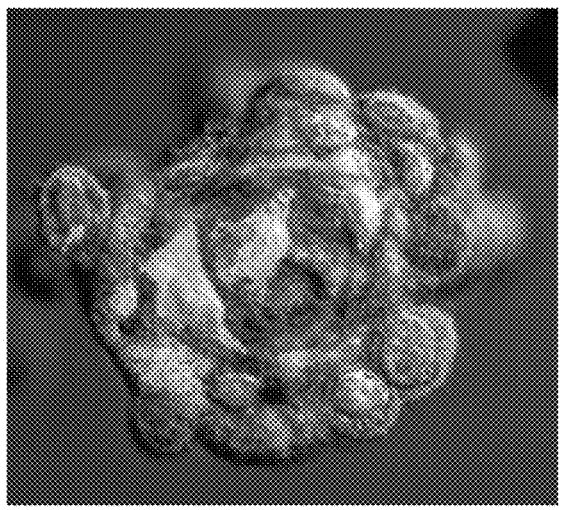
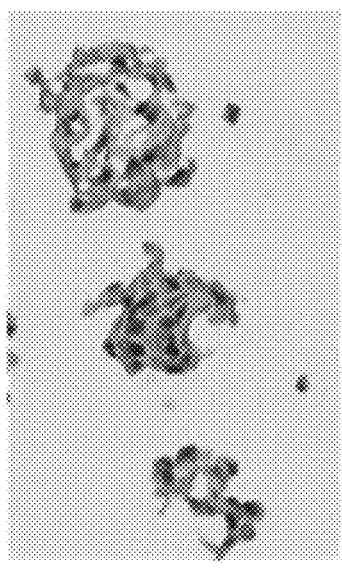
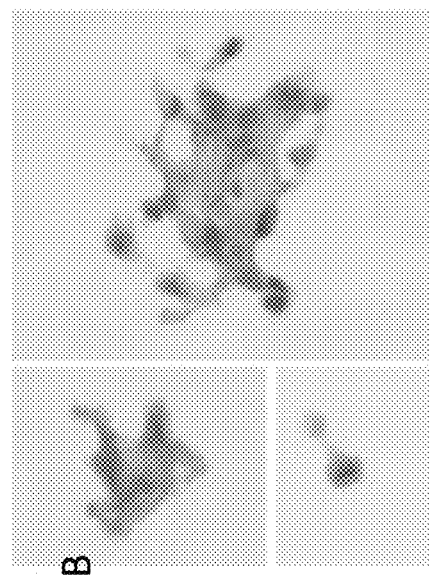
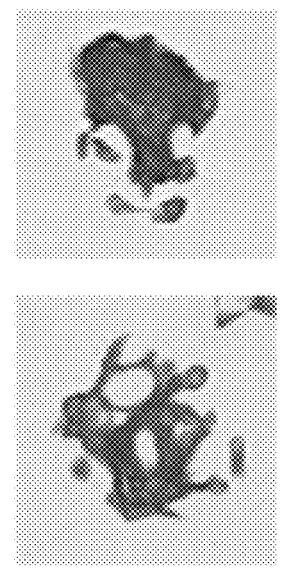
FIG. 9A
FIG. 9B
FIG. 9C
FIG. 9D
FIG. 9E
FIG. 9F

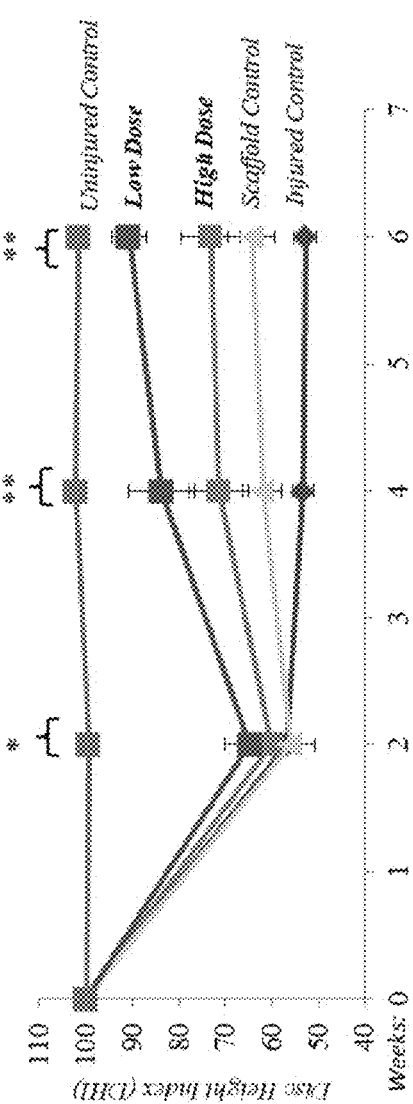
FIG. 12B
FIG. 12C
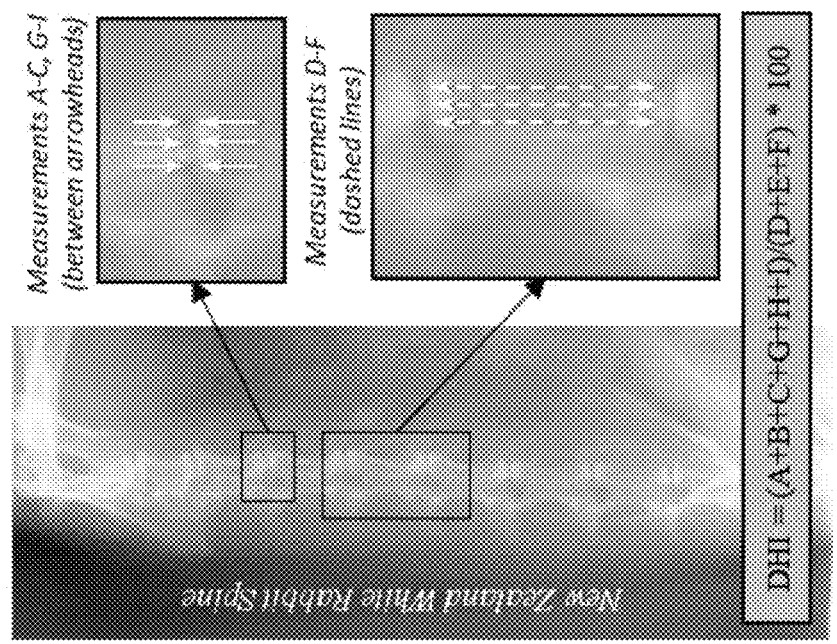
FIG. 12A

 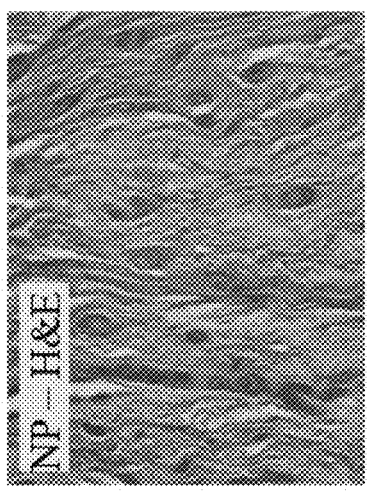 
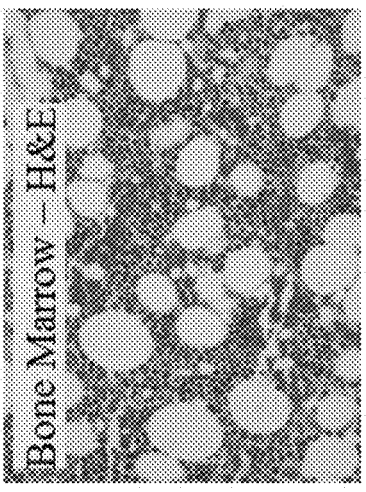 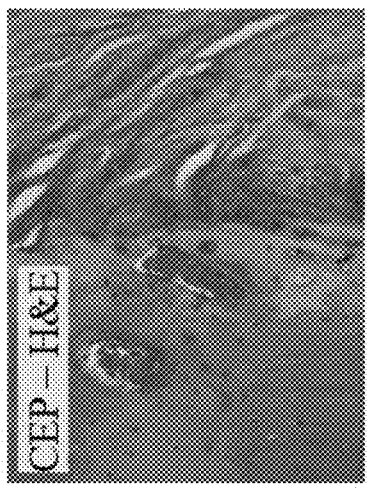 
FIG. 13B
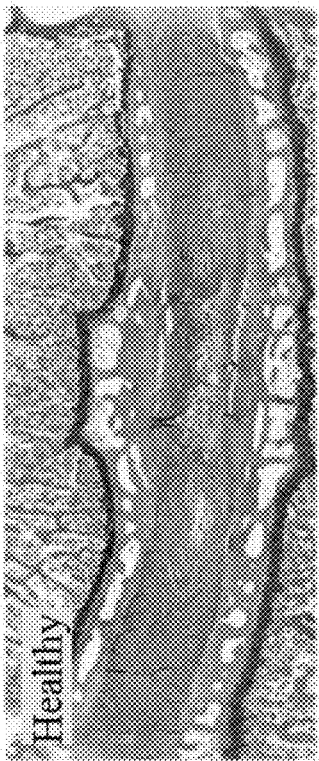 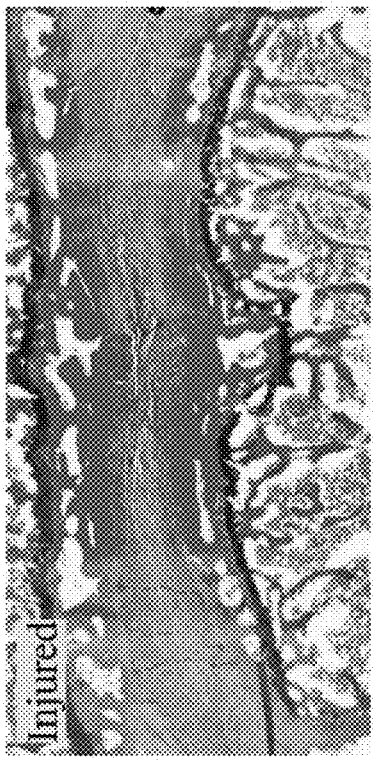 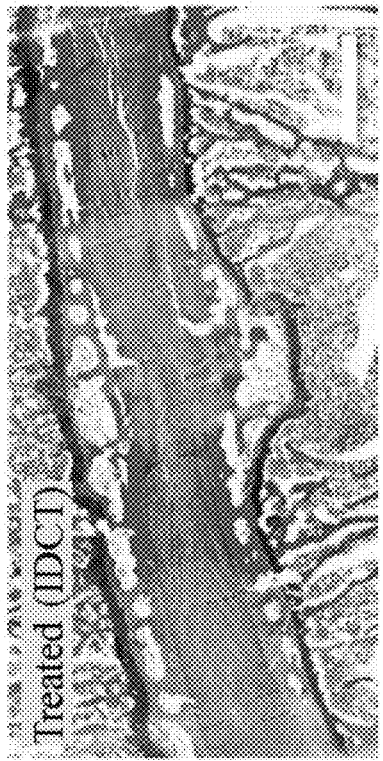
FIG. 13A FIG. 14B
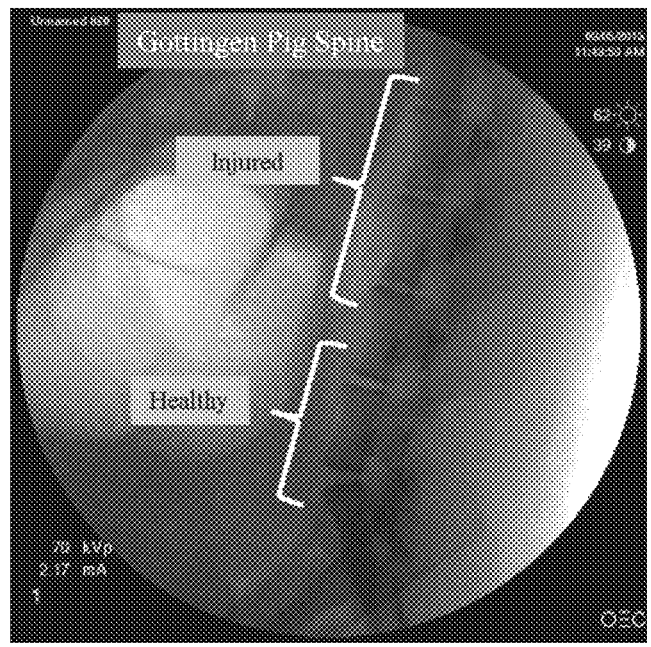
FIG. 14C
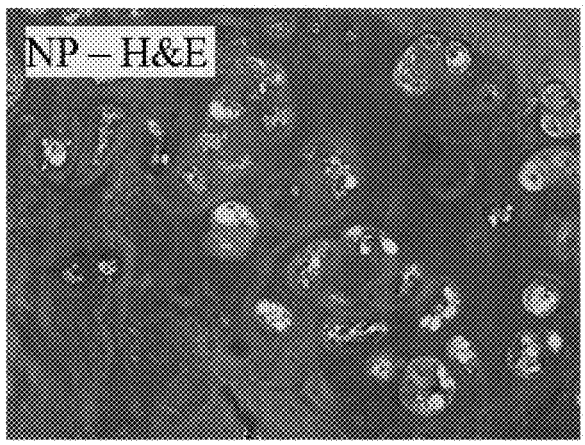
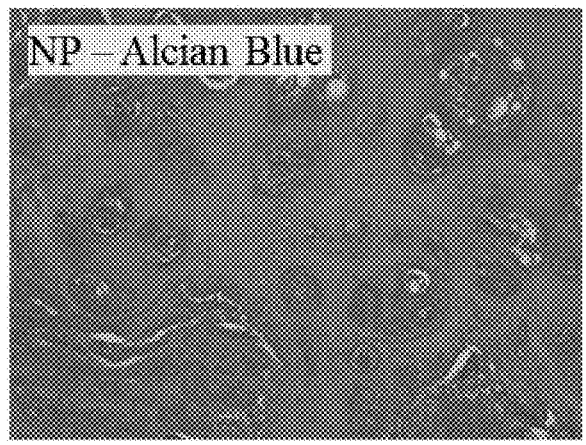
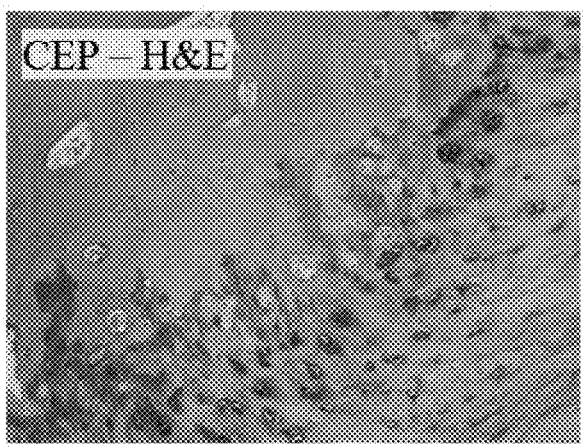

ISOLATED DISCOGENIC CELLS, METHODS OF USING, AND METHODS OF PREPARING SAME FROM MAMMALIAN TISSUE

CROSS REFERENCE TO RELATED APPLICATIONS

This application claims benefit of priority pursuant to 35 U.S.C. § 119(e) of U.S. provisional patent application No. 61/794,691 filed Mar. 15, 2013, which is hereby incorporated herein by reference in its entirety.

FIELD OF INVENTION

This disclosure relates to the isolation and methods of using intervertebral disc cells in the treatment of degenerative disc disease.

BACKGROUND OF THE INVENTION

The mammalian spine serves two basic functions: (1) load bearing support for the upper body and (2) protection of the nerves comprising the spinal column. The spine is made up of interlocking vertebrae, separated by intervertebral discs. These discs act as shock absorbers and allow the spine to bend, compress, and twist. Spinal discs have two basic parts: an outer fibrous structure (the annulus fibrosus), and a gel-like inner structure (the nucleus pulposus). A healthy nucleus pulposus in a young mammal is about 80% water. Over time, the nucleus pulposus loses its high water content and thus its ability to absorb shock. Additionally, intervertebral discs can be damaged through dehydration, disease, over-use, injury or trauma, resulting in rupture, bulging, herniation, etc. The intervertebral disc is also susceptible to other diseases such as degenerative disc disease.

In a healthy intervertebral disc, cells represent a small fraction of the total volume. Much of the disc volume is extracellular matrix (ECM; collagen and proteoglycans, which aid in retaining the large volume of water) produced by the cells, and much of the difference between the nucleus pulposus and annulus fibrosus is the water content and the makeup of the ECM.

Back pain resulting from degenerative disc disease is a major cause of morbidity, disability, and lost productivity. Back pain is frequently cited as limiting the activity of people under the age of 45 and a reason for physician visits, hospitalization, and surgical procedures. Chronic back conditions are reported by between 15%-45% of the population each year, and in 70% to 85% of the population at some time in their lives. The financial impact in terms of health care dollars and lost work hours to society is high. More than one million spine surgery procedures are performed annually in United States. Furthermore, the lumbar fusion segment of the spine surgery market is estimated at well over $1 billion in annual revenue.

Despite continued improvements in both operative and non-operative treatment options for subjects suffering from back pain and spine disease, there is no solution to eliminate or consistently improve this condition. Current treatments for spine disease include steroid injections, physical therapy, discectomy and spinal fusions. Spinal prostheses have been introduced by several companies. However, these prostheses differ greatly in their design, for example in the bearing surface, fixation to bone, number of articulations, material, constraint, mobility of rotation, and have seen little success in practice.

Nucleus arthroplasty or nucleus replacement is also an option for treating degenerative disc disease. In some cases, these devices consist of a hydrogel core center encased in a polyethylene sleeve that allows the device to shrink and swell during normal loading and unloading. This may partially help restore disc space height and aid in mimicking healthy human disc.

Disc arthroplasty is not without complications. The most common complications include adjacent level spinal disease, subsidence, and facet joint arthrosis. Furthermore, recent studies from clinical trials have demonstrated incidences of infection, vertebral body fracture, implant malposition, subsidence, mechanical failure, and paravertebral heterotopic ossification. More serious complications, including anterior dislocation of the implant, have been reported. Also, the issue of wear particles from the total disc arthroplasty and the potential effects on the spinal cord are still not known.

What is needed is a biologic treatment for intervertebral discs that can aid in repairing or replacing a subject's intervertebral disc.

SUMMARY OF THE INVENTION

Disclosed herein are isolated discogenic cell populations, methods of using, and methods of preparing. The discogenic cell populations are used in the repair, regeneration, and replacement of damaged, injured, or diseased intervertebral discs. In some embodiments the discogenic cell population is derived from mammalian disc tissue and grown in vitro under anchorage independent conditions. In some embodiments the cells the culture comprises a media comprising one or more additives selected from the group consisting of EGF, bFGF, serum, fibroblast conditioned media, and a viscous non-reactive substance. In some cases, the cells are grown in a receptacle comprising a low adhesion coating. The disclosed discogenic cell populations may be used for autologous and/or non-autologous treatment of intervertebral disc in a subject in need thereof.

The disclosed discogenic cells can be used to produce an artificial disc replacement in vitro or in vivo using non-resorbable material or resorbable material. The material may create an artificial annulus that serves to contain a discogenic cell population, which may or may not be combined with at least one of the following—scaffold material, matrix material, carrier material, growth factor(s), and/or other biologically active agents. The artificial outer annulus may incorporate attachment means so that it can be fixed to one or more vertebral bodies. For example, the artificial annulus may incorporate through-holes, cuffs, tabs, loops, or washers to allow for screw fixation to one or more vertebral bodies. The artificial disc can be surgically implanted in a subject to completely replace a spinal disc.

Also disclosed are various methods for obtaining and preparing discogenic cells from autologous and non-autologous donors. A method of deriving a discogenic cell population is disclosed wherein the method comprises isolating one or more cells from tissue, passaging the one or more cells in an anchorage dependent culture media, and transferring the one or more cells to an anchorage independent culture media. Another method is disclosed using a discogenic cell to treat at least one disc in a subject in need thereof comprising, administering a therapeutic amount of a discogenic cell population to the subject, and thereby treating the subject. In various embodiments, the tissue is mammalian disc tissue, for example from a donated organ or spine. In some aspects, the disclosed method includes wherein the cell population is passaged at least one time in the anchorage independent culture, and the population of cells produces extracellular matrix. In some aspects the population of cells produces one or more cell surface markers selected from the group comprising CD24, CD34, CD44, CD73, CD90, CD105, CD166, Stro-1, HIF1, nestin, CK8, and HLA proteins, wherein the percentage of the cells in the population expressing a cell surface marker(s) is greater than 70% or less than 40%. In some aspects of the disclosed method the population of cells expresses one or more gene or gene products selected from the group comprising GAPDH, SDHA, HPRT1, B2M, Sox9, Aggrecan, Col1, Col2, nestin, CK8, Sox1, CD44, ALPI, PPARG, ADAMTS, MMP, FMOD, IL.

In another aspect, a population of Discogenic cells is described, wherein greater than 40% of the cells produce cell surface markers CD44, CD73, CD90, HLA-A, B, or C, CD24, CD105, CD166, or combinations thereof, and less than about 20% of the cell population produces CD34, HLA-DR or -DQ, or STRO-1. In some embodiments, about 80-100% of the population produces CD73, CD90, CD44, HLA ABC, or combinations thereof. In some embodiments, about 20-75% of the population produces CD105, CD166, CD24, or combinations thereof.

In accordance with one aspect, the invention provides methods for treating a subject having a disease of or damage to at least one intervertebral disc caused by damage to the intervertebral disc induced by age, trauma, toxin exposure, drug exposure, radiation exposure, oxidation, immune-complex deposition, or transplant rejection.

In accordance with another aspect, the invention provides kits for treating a subject having a disease of or damage to at least one intervertebral disc, comprising a pharmaceutically acceptable carrier, discogenic cells in an amount effective to treat the disease or injury, spinal column tissue and wherein the cells are capable of expansion in culture and have the potential to differentiate. In some embodiments, the kit includes at least one agent.

BRIEF DESCRIPTION OF THE DRAWINGS

The file of this patent contains at least one drawing/photograph executed in color. Copies of this patent with color drawing(s)/photograph(s) will be provided by the Office upon request and payment of the necessary fee.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 1A-B show expression profiles of various surface markers known to identify stem cells and chondrogenic cells. Eight cell types are explored: fibroblasts, chondrocytes, mesenchymal stem cells (MSCs), discogenic cells grown in monolayer (attachment dependent), and discogenic cells grown in suspension (attachment independent).

FIGS. 4A-B show the adipogenic and osteogenic potential of discogenic cells.

FIG. 8 (including FIGS. 8A-F) is a schematic flow chart showing preparation and implantation of discogenic cells. Step a shows a diagram of an intervertebral disc. Step b shows fresh human intervertebral disc isolated from a spine. Step c shows nucleus pulposus cells after dissected and enzymatic digestion. Cells that adhere are expanded in the presence of EGF and FGF-2. Scale bar=50 µm. Step d is a micrograph of cells transitioned to a contact-inhibited culture environment containing methylcellulose, wherein clusters and spheres develop over about 2 weeks. Scale bar=200 µm. Step e is a syringe for injecting cells that have been washed free of methylcellulose-containing media and combined with uncross-linked hyaluronic acid scaffold. Step f shows the syringe being used to inject the mixture of cells and scaffold is into degenerated rabbit intervertebral discs, afterward, the safety and efficacy was assessed for about 1 month.

FIGS. 9A-F shows discogenic cells assessed for Aggrecan and Collagen production. FIG. 9A is a phase image of hematoxylin and eosin staining. FIG. 9B is a phase image of alcian blue counterstained with nuclear fast red. Note presence of matrix around single cell (left). Scale bar=10 um. FIG. 9C is a phase image of picrosirius red staining. FIG. 9D is a confocal image including actin (red) and cell nuclei (blue). FIG. 9E is a confocal image for aggrecan, collagen and actin (no nuclei) with additional magnification, wherein the black arrow indicates intracellular aggrecan, and the white arrow indicates extracellular aggrecan. FIG. 9F is a bar graph showing RT-PCR analysis of matrix molecules (aggrecan and collagen 2A) over time in culture, at day 14 harvest and after chondrogenic differentiation. Fold expression was calculated by normalized crossing threshold to housekeeping gene HRPT and baseline gene expression at day 0.

FIG. 10A is a forward and side scatter plot, showing gating applied to all subsequent analyses that includes 89% of the cell population. FIG. 10B is a bar graph showing expression levels (compared to isotype control) of discogenic cells from 5 distinct human donors. FIG. 10C shows representative histograms of surface marker expression.

FIG. 11A shows osteogenic differentiation shown with alizarin red staining. FIG. 11B shows adipogenic differentiation shown with oil red O staining. FIG. 11C shows chondrogenic differentiation after micromass formation (alcian blue and nuclear fast red). Scale bars=100 um. FIG. 11D is a bar graph showing quantitative evaluation of soluble (media) and insoluble (micromass) GAG production after chondrogenic differentiation for articular chondrocytes (AC), adult fibroblasts (FB), bone marrow derived MSCs, and discogenic cells (DCs). FIG. 11E is a bar graph showing total GAG production normalized to DNA content for various cell types. Line indicates significant difference ($p<0.01$, 1-way ANOVA with Bonferroni's post-hoc test).

FIGS. 12A-C show safety and efficacy assessments of treatment in a rabbit model of degenerative disc disease. FIG. 12A is a representative x-ray, which were taken every 2 weeks and used to calculate disc height index (DHI) based on 18 boney landmarks, as shown. FIG. 12B shows that rabbit body weight (therapy injected on day 14) for the duration of the study remained within normal ranges. FIG. 12C is a graph DHI over the 6 week treatment showing that reatment improved DHI compared to control conditions after 4 and 6 weeks, with low dose performing better than high dose. No improvement as noted in scaffold or injured control, whereas uninjured control disc height remained unchanged from week 0.

FIGS. 13A-B show histological evaluation of treatment after 6 week Pilot Study. FIG. 13A is a cross-section of a healthy, injured and treated disc (Hematoxlyn and eosin stain, scale bar=2 mm. FIG. 13B shows histology of various regions of the IVD after treatment, including bone marrow, annulus fibrosus (AF), cartilage endplate (CEP), and nucleus pulposus (NP); stained with hematolxyin and eosin (H&E) or alcian blue. (Scale bar=100 um).

FIGS. 14A-C show pilot safety and efficacy of treatment in pigs (12 weeks) FIG. 14A is a graph showing that doses of IDCT improved DHI compared to injured control ($p<0.05$) in a sustained manner at 12 weeks; no improvement noted in scaffold or injured control, whereas uninjured control disc height remained unchanged from week 0. FIG. 14B is a fluoroscopic view of pig spine during treatment procedure (note collapsed disc space in injured discs). FIG. 14C is a histological evaluation of IDCT-treated discs, including nucleus pulposus (NP), cartilage endplate (CEP) and annulus fibrosus (AF) stained with Hemtoxylin and eosin (H&E) and alcian blue.

DETAILED DESCRIPTION OF THE INVENTION

Figure 1B:
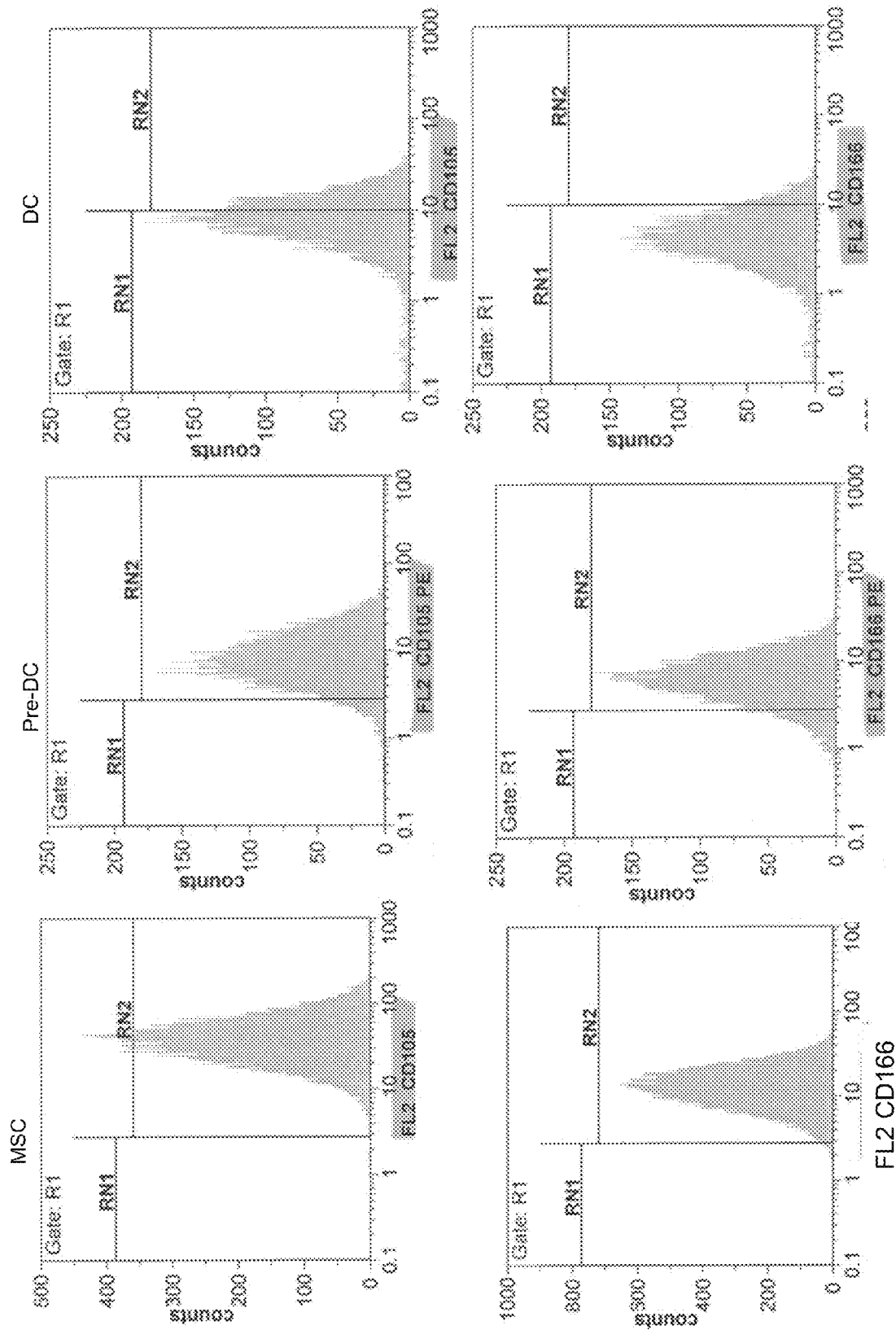

The presently described discogenic cells are cells that are derived from disc tissue and may be used for the treatment and/or repair of intervertebral discs. In some cases, discogenic cells may be processed in vitro to provide for discogenic cells that are more potent than other cells in repairing, replacing, or augmenting existing or damaged nucleus pulposus tissue. In various embodiments discogenic cells produce extracellular matrix. In some embodiments, discogenic cells produce proteoglycans. In other embodiments, discogenic cells produce collagens. In other embodiments, discogenic cells implanted adjacent native cells may aid in stimulating native cells through chemical, mechanical or other forces. For example, discogenic cells may excrete growth factors, cytokines or other proteins.

"Discogenic," as used herein, refers to the ability to produce disc tissue in vivo. In some embodiments, discogenic cells are able to regenerate disc tissue that is diseased or damaged and/or has lost one or more properties of disc tissue in vivo. In some cases, "discogenic" cells may produce disc tissue in vitro, for example where discogenic cells may be used to generate an artificial disc for implantation.

"Maintained" as used herein where referring to cells grown in-vitro, is meant to encompass cells grown in culture for greater than 24 hours. In some cases, maintained cells are cells that have divided in cell culture.

"Micromass" is formed by concentrating about 10,000 to 1,000,000 cells in a conical vessel that inhibits attachment, which results in cells forming a least one singular mass. The micromass may additionally contain extracellular matrix. It is based upon an assay to determine chondrogenic potential, and is also known as a pellet.

"About" as used herein when referring to a measurable value such as an amount, a temporal duration, and the like, is meant to encompass variations of less than about ±20%. In some cases about may refer to variations of 10% or less, or ±5% or less. In some cases about may refer to variation of ±1%-±0.1%.

"Derived" may be used to indicate that a cell has been obtained or isolated from its natural or previous biological state or situs and maintained, grown or expanded in culture, or immortalized, or otherwise manipulated in vitro. For example, in some present embodiments, the disclosed discogenic population may be derived from disc tissue or cartilaginous tissue, and in some embodiments discospheres may be derived from a discogenic cell population.

If a cell or molecule is "isolated" it has been removed from, or altered in relation to its natural state through human intervention.

The term "express," "expressed," or "expression" refers to the biosynthesis of a gene product from a nucleic acid molecule or gene, for example, the biosynthesis of a polypeptide. A cell surface marker may be expressed on the surface of a cell if more or less of that cell marker is present on the surface of the cell after some event, for example growth in vitro.

"Damage" refers to any harm, injury, degeneration, or trauma to the intervertebral disc whether due to age, trauma, or disease.

A "disease" is any deviation from, or impairment in the health, condition, or functioning of a cell, tissue, organ, system, or organism on the whole, as measured by any means suitable in the art.

"Treat," treating" or "treatment" refer to any attenuation or amelioration of disease, damage, or condition, including any objective or subjective parameter such as abatement, remission, diminishing of symptoms or making the disease, damage, or condition more tolerable to a subject, for example through pain reduction), slowing in the rate of degeneration or decline, making the final point of degeneration less debilitating, improving a subject's physical or mental well-being, or prolonging the length of survival. The treatment or amelioration of symptoms can be based on objective and/or subjective parameters; including the results of a physical examination, radiographic examination, neurological examination, and/or psychiatric evaluations.

"Effective amount" or "therapeutically effective amount" are used interchangeably herein, and refer to an amount of a compound, material, or composition, as described herein effective to achieve a particular biological result such as, but not limited to, biological results disclosed, described, or exemplified herein. Such results may include, but are not limited to, the treatment of intervertebral disc disease or damage in a subject, as determined by any means suitable in the art.

"Pharmaceutically acceptable" refers to those properties and/or substances which are acceptable to the subject from a pharmacological/toxicological point of view and to the manufacturing pharmaceutical chemist from a physical/chemical point of view regarding composition, formulation, stability, subject acceptance and bioavailability.

"Pharmaceutically acceptable carrier" refers to a medium that does not interfere with the effectiveness of the biological activity of the active ingredient(s) and is not toxic to the host to which it is administered. One embodiment of a pharmaceutically acceptable carrier is hyaluronic acid.

"Discosphere" is described in U.S. Pat. No. 8,227,246 B2 and PCT application number PCT/US2012/025066, which are hereby incorporated by reference in their entireties.

Obtaining Discogenic Cells from Disc Tissue

The presently described discogenic cells may be obtained from disc tissue. Disc tissue may include both nucleus pulposus tissue, transition zone tissue, and annulus fibrosis tissue. In some cases, discogenic cells may be obtained from cartilaginous endplate of the intervertebral disc. In other cases, discogenic cells may be obtained from other cartilaginous tissues in the body.

In various embodiments the disc tissue may be obtained from living or deceased donors. The donor may be a mammal, for example a human. In some cases, the donor is a tissue donor and may be genetically unrelated to the recipient. The donor may be of any age, including neonatal, young, adult and senior.

In various embodiments the disc tissue may be healthy disc tissue or may be diseased or injured disc tissue. Injured or diseased disc tissue that may be used with the currently disclosed discogenic cells and methods include, for example, degenerated tissue, herniated tissue, tissue removed from painful discs, tissue removed from deceased donors.

In various embodiments, the tissue is used directly to obtain cells. In other embodiments, the tissue is frozen prior to use, and used at a later date, for example by cryopreservation or vitrification. In other embodiments, the tissue is kept at 4° C. in specialized media until the cells are extracted. Tissue can be maintained in media, containing sugars, cryoprotectants, stabilizers, serum, etc.

Culturing Discogenic Cells

Discogenic cells may be grown in mammalian cell culture. In most cases, the cell culture may allow anchorage to a substratum, or alternatively prevent anchorage to a substratum. In some cases, the cell culture may include a medium. Cell culture media may be any media suitable for the growth of mammalian cells in culture, for example DMEM (Dulbecco's Modified Eagle's Medium), MEM (Modified Eagle's Medium), RPMI, RPMI 1640, etc. In some cases, the media may additionally include further additives such as a nutrient media, for example Ham's F12 (F12). In some case, the cell culture media may or may not include further additives.

In various embodiments, serum may or may not be added to the culture media. Serum may refer to animal serum derived from a mammal, for example, cow, chicken, goat, equine, human, sheep, pig, rabbit, etc. In some cases, the serum may be derived from adult, newborn, or fetal animals, for example fetal bovine serum may be obtained from a cow or calf fetus. In some cases, a serum additive such as animal platelet lysates (for example, human platelet lysates), serum-converted platelet lystate, animal serum albumin (bovine serum albumin), or conditioned media from another cell culture (for example neonatal foreskin fibroblast conditioned media) may be added with, or in the place of serum.

In some cases, the serum or serum additive concentration in the culture media may be greater than 0%, 1%, 2%, 3%, 4%, 5%, 6%, 7%, 8%, 9%, 10%, 11%, 12%, 13%, 14%, 15%, 16%, 17%, 18%, 19%, 20%, 25%, and 30%, and/or less than about 35%, 30%, 25%, 20%, 19%, 18%, 17%, 16%, 15%, 14%, 13%, 12%, 11%, 10%, 9%, 8%, 7%, 6%, 5%, 4%, 3%, 2%, and 1% by volume. In some cases the serum concentration in the media may be 0%. In some embodiments the serum concentration is from 0-17%, 0-5%, 5-17% or 0-2.5%.

In some cases, additional supplements may or may not be added to the culture media. In some cases, the supplement may be a hormone or growth factor. In some cases the hormone or growth factor may be Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), basic Fibroblast growth factor (bFGF, FGF-2, or FGF-β), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha (TGF-α), Transforming growth factor beta (TGF-β), Tumor_necrosis_factor-alpha (TNF-α), Vascular endothelial growth factor (VEGF), placental growth factor (PlGF), IL-1, IL-2, IL-3, IL-4, IL-5, IL-6, IL-7, insulin, progesterone, putrescine, transferrin, sodium selenite. In many cases, the growth factors may be EGF and bFGF. In many cases the concentration of supplement in the cell culture media may be greater than about 1 ng/ml, 2 ng/ml, 3 ng/ml, 4 ng/ml, 5 ng/ml, 6 ng/ml, 7 ng/ml, ng/ml, 9 ng/ml, 10 ng/ml, 11 ng/ml, 12 ng/ml, 13 ng/ml, 14 ng/ml, 15 ng/ml, 20 ng/ml, 25 ng/ml, 30 ng/ml, 35 ng/ml, 40 ng/ml, 50 ng/ml, 100 ng/ml, 200 ng/ml, 300 ng/ml, 400 ng/ml, 500 ng/ml, 600 ng/ml, 700 ng/ml, 800 ng/ml, 900 ng/ml, 1 µg/ml, 10 µg/ml, 20 µg/ml, 30 µg/ml, 40 µg/ml, 50 µg/ml, 60 µg/ml, 70 µg/ml, 80 µg/ml, 90 µg/ml, 100 µg/ml, 200 µg/ml, 300 µg/ml, 400 µg/ml, 500 µg/ml, 600 µg/ml, 700 µg/ml, 800 µg/ml, 900 µg/ml, and 1 mg/ml and/or less than about 1.1 mg/ml, 900 µg/ml, 800 µg/ml, 700 µg/ml, 600 µg/ml, 500 µg/ml, 400 µg/ml, 300 µg/ml, 200 µg/ml, 100 µg/ml, 90 µg/ml, 80 µg/ml, 70 µg/ml, 60 µg/ml, 50 µg/ml, 40 µg/ml, 30 µg/ml, 20 µg/ml, 10 µg/ml, 9 µg/ml, 8 µg/ml, 7 µg/ml, 6 µg/ml, 5 µg/ml, 4 µg/ml, 3 µg/ml, 2 µg/ml, 1 µg/ml, 900 ng/ml, 800 ng/ml, 700 ng/ml, 600 ng/ml, 500 ng/ml, 400 ng/ml, 300 ng/ml, 200 ng/ml, 150 ng/ml, 100 ng/ml, 50 ng/ml, 40 ng/ml, 35 ng/ml, 30 ng/ml, 25 ng/ml, 20 ng/ml, 16 ng/ml, 15 ng/ml, 14 ng/ml, 13 ng/ml, 12 ng/ml, 11 ng/ml, 10 ng/ml, 9 ng/ml, 8 ng/ml, 7 ng/ml, 6 ng/ml, 5 ng/ml, 4 ng/ml, 3 ng/ml, 2 ng/ml, and 1 ng/ml. In some cases the concentration of supplement may be greater than 1 nM, 2 nM, 3 nM, 4 nM, 5 nM, 6 nM, 7 nM, nM, 9 nM, 10 nM, 11 nM, 12 nM, 13 nM, 14 nM, 15 nM, 20 nM, 25 nM, 30 nM, 35 nM, 40 nM, 50 nM, 100 nM, 200 nM, 300 nM, 400 nM, 500 nM, 600 nM, 700 nM, 800 nM, 900 nM, 1 µM, 10 µM, 20 µM, 30 µM, 40 µM, 50 µM, 60 µM, 70 µM, 80 µM, 90 µM, 100 µM, 200 µM, 300 µM, 400 µM, 500 µM, 600 µM, 700 µM, 800 µM, 900 µM, and 1 mM and/or less than about 1.1 mM, 1 mM, 900 µM, 800 µM, 700 µM, 600 µM, 500 µM, 400 µM, 300 µM, 200 µM, 100 µM, 90 µM, 80 µM, 70 µM, 60 µM, 50 µM, 40 µM, 30 µM, 20 µM, 10 µM, 9 µM, 8 µM, 7 µM, 6 µM, 5 µM, 4 µM, 3 µM, 2 µM, 1 µM, 900 nM, 800 nM, 700 nM, 600 nM, 500 nM, 400 nM, 300 nM, 200 nM, 150 nM, 100 nM, 50 nM, 40 nM, 35 nM, 30 nM, 25 nM, 20 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, and 1 nM. In some cases the concentration is about 5-110 ng/ml, 5-15 ng/ml, or 90-110 ng/ml.

In some case the cell culture media may or may not comprise a neuronal supplement. In some cases, the neuronal supplement may be a commercial neuronal supplement, for example B27, N2, or N10. In cases where a neuronal media supplement is added, the concentration of supplement in the cell culture media may be greater than about 0×, 1×, 2×, 3×, 4×, and 5×, and/or less than about 10×, 6×, 5×, 4×, 3×, 2× and 1×. Other commercial products include NeuroCult, ANS Neural Media supplement, Neurobasal supplement, B28, NS21, G5, N21, NS21, etc.

In some cases, the cell culture media may also include other chemicals, molecules, supplements, or additives known to one of skill in the art of mammalian cell culture, for example, amino acids, peptides, salts, vitamins, antibiotics, antimycotics, antifungals, minerals, pH buffers, pH indicators, and sugars. In many cases the pH of the cell culture media may be greater than about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, and 7.9 and/or less than about 8.0, 7.9, 7.8, 7.7, 7.6, 7.5, 7.4, 7.3, 7.2, 7.1, 7.0, 6.9, 6.8, 6.7, 6.5, 6.6, 6.4, 6.3, 6.2, 6.1, and 6.0. In various embodiments, the pH is from about 6.9-7.7, 7.0-7.4, or 7.3-7.7.

Discogenic cells may be grown in a monolayer or in suspension. In some cases, cells may be grown in cell sterile receptacles, such as plates, dishes, flasks, roller flasks, and reactors for mammalian cell culture, which allow for the exchange of gases and medium as needed. In various embodiments, cells may be grown while the receptacle may be stationary, or moving, for example by rotation or rolling of the receptacle. In some cases, the cell culture media may be agitated, for example by rotation, rocking, or rolling of the receptacle. The cell culture media may also be agitated through other processes, for example physical movement of the cell culture media in a stationary receptacle, by, for example a stir rod, stir bar or other mechanical stirring mechanism within the cell culture media. In some cases the receptacle may include baffles for aiding in agitation of the media.

In some cases, the receptacle may be treated, for example to aid or inhibit cell attachment. Various culture methods may be used to grow cells under anchorage independent conditions. In general, cells that are able to grow in suspension may be grown in anchorage independent conditions. For example, cells that can grow and divide without attachment to a substratum may be anchorage independent. In some cases the receptacle may be coated to aid in attachment, for example with gelatin or collagen. In some cases the receptacle may be coated to inhibit cells adhering or attaching to the receptacle surface, for example ultra-low attachment surface modifications. In some cases, receptacles may be commercially available, for example ultra-low attachment receptacles (Corning). Further, viscous non-reactive media additives, such as methylcelluose, poloxmer, or agar/agarose, may or may not be used to maintain a free-floating suspension of cells.

In some cases, where the cell culture media is supplemented to prevent or inhibit cell attachment, for example where a viscous, non-reactive substance is added, the concentration of the additive in the cell culture media may be greater than about 0.1%, 0.2%, 0.3%, 0.4%, 0.5%, 0.6%, 0.7%, 0.8%, 0.9%, 1.0%, 2%, 3%, 4%, 5%, 6%, 7%, 8%, 9%, 10%, and 15% and/or less than about 20%, 15%, 10%, 9%, 8%, 7%, 6%, 5%, 4%, 3%, 2%, 1.0%, 0.9%, 0.8%, 0.7%, 0.6%, 0.5%, 0.4%, 0.3%, 0.2%, and 0.1%. The final concentration of viscous reagent may depend on the reagent used, for example where methylcellulose is used the concentration may be between about 0.6-0.9%, 0.7-0.8%, or 0.75%. Where agarose is used, the concentration may be from about 1-5%, 2-4%, or 3%.

In some cases, discogenic cells may be grown in atmospheres that have ambient levels of oxygen or higher or lower levels of oxygen. In many cases ambient levels of oxygen may be between 22 and 19% oxygen. In some case the atmosphere that the cells are grown in has less than 22%, 21%, 20%, 19%, 18%, 17%, 16%, 15%, 14%, 13%, 12%, 11%, 10%, 9%, 8%, 7%, 6%, and 5%, and/or greater than about 4%, 5%, 6%, 7%, 8%, 9%, 10%, 11%, 12%, 13%, 14%, 15%, 16%, 17%, 18%, 19%, 20%, 21%, 22%. In some embodiments where hypoxia is desired the concentration of oxygen may be about 3-7%, 4-6%, 5% or 6%.

Surface Markers

In some cases, discogenic cell populations may be characterized by the expression of cell-surface markers. In some cases the population of discogenic cells may or may not express one or more specific cell surface markers and/or cluster of differentiation proteins. In various embodiments, a population of discogenic cells may have a higher or lower percentage of gated cells with a specific marker than does a reference cells, for example a chondrocyte or a adipocyte. In other cases, a population of discogenic cells may have a percentage of gated cells with a cell surface marker. In some cases the percentage of gated cells having a specific cell surface marker is greater than 40%, 50%, 60%, 70%, 80%, and 90%, and/or less than about 100%, 90%, 80%, 70%, 60%, and 50%.

Cell surface markers that may aid in characterizing a discogenic cell population may include, without limitation, CD24, CD34, CD44, CD73, CD90, CD105, CD166, Stro-1, HIF1, nestin, CK8, and HLA proteins (Human Leukocyte Antigen, e.g. HLA-A, -B, -C, HLA-DQ, and HLA-DR). In some cases, CD24 may be a glycoprotein expressed at the cell surface (e.g. lymphocytes, granulocytes, and neuroblasts), anchored via a glycosyl phosphatidylinositol (GPI) link to the cell surface. CD24 may also be referred to as Heat Stable Antigen (HSA). CD44 may refer to a cell-surface glycoprotein involved in cell-cell interactions, cell adhesion and migration. CD73 may also be referred to as 5'-ribonucleotide phosphohydrolase, and expressed on, for example B-cells, T-cells, endothelial cells, pericytes, follicular dendritic cells, fibroblasts, epithelial cells, cardiomyocytes, neurons, osteoblasts, trophoblasts and mesenchymal stem cells (MSCs). CD90 may refer to the glycoprotein Thy-1 Thymus cell antigen. CD105 may refer to Endoglin, a glycoprotein component of the TGF-beta receptor complex. CD166 may refer to activated leukocyte cell adhesion molecule (ALCAM). Stro-1 may refer to a marker of immature mesenchymal stem cells. HIF-1 may refer to hypoxia inducible factor. Nestin may refer to a neural marker. CK8 may refer to a cytokeratin marker.

In some cases, expression of cell surface proteins/markers on discogenic cells may be measured. In various embodiments, cell surface protein expression is measured by using fluorescent antibodies that recognize an epitope of the cell surface protein being measured. In some cases, the measurement is through the use of flow cytometry, including fluorescence-activated cell sorting (FACs), using standard techniques. As measured by FACs, the expression is measured as a percentage of gated cells within a specified range, where gating is set using IgG controls. In some cases, expression is greater than about 70% for HLA-ABC, CD44, CD73 and CD90, and below 40% for CD24, CD105 and CD166.

Additionally, in some cases surface markers may be used to sort, isolate or concentrate a specific subpopulation or cells. For example, cell sorting using magnetic beads, fluorescent markers or other techniques may be used to select subpopulations within the population.

Gene Expression

Additional to surface markers, in some cases genomic and genetic analysis is used to identify the discogenic cells. Techniques include quantitative polymerase chains reaction, microarray analysis, western blot, etc. Expression of genes via measurements of DNA, mRNA, miRNA or protein, measured by fold-increase or decrease against house-keeping genes (GAPDH—Glyceraldehyde 3-phosphate dehydrogenase, SDHA—Succinate dehydrogenase complex, sub-unit A, HPRT1—hypoxanthine phosphoribosyltransferase, B2M—Beta-2 microglobulin, etc), may be used to identify discogenic cells, such as transcription factor Sox9, extra-cellular matrix component aggrecan, extra-cellular matrix components collagen 1 and 2, neural marker nestin, cytokeratin 8, transcription actor Sox 1, CD44 (a receptor for hyaluronic acid), ALPI (alkaline phosphatase), PPARG (peroxisome proliferator-activated receptor gamma), MMP (matrix metalloproteinase), ADAMTS (A disintegrin and metalloproteinase with thrombospondin motifs), FMOD (fibromodulin), interleukins, etc.

Cryopreservation

In some cases, cells may be cryopreserved. Cells may be combined with preformulated cryopreservation media, such as Cryostor, HyCryo, UltraCruz, Cyagen, etc. Or, cells may be combined with formulated cryopreservation media, which may or may not contain serum, albumin, dimethyl sulfoxide, trehalose, sucrose, other sugars, ethylene glycol, glycerol, propylene glycol, hyaluronic acid, collagen, matrigel, other natural extra-cellular matrix molecules etc. Cells may be frozen rapidly (vitrification) or slowly (defined timecourse in various temperatures, or controlled-rate freezing machine). Cells may be frozen from 0.1-10 million cells/mL.

Isolating Discogenic Cell Populations

Methods of deriving, obtaining, or isolating discogenic cells from disc tissue are described. In some cases the isolated discogenic cell population is derived from autologous or non-autologous donors. An autologous donor may be where the discogenic cell population is derived from subject to be treated with the cells. A non-autologous donor, also known as an allogeneic donor, may be a different subject. Also disclosed are various methods for obtaining and preparing discogenic cells from living and or deceased donors.

In most cases, the method of isolating discogenic cells from disc tissue comprises separating disc cells from extra-cellular matrix. In some cases, disc tissue may be broken up mechanically, chemically, and/or enzymatically. In some cases disc tissue may be chopped, sliced, or minced. In some cases, disc tissue is treated with an enzyme, for example collagenase. The treatment of disc tissue may aid in removal of extracellular matrix. In some cases, the tissue is placed in tissue cultured-treated dishes with direct contact to the surface of the dish with media, and the cells migrate from the tissue and onto the plate. In other cases, the cells are separated from the tissue using a filter.

Extracellular matrix may comprise collagen, proteoglycans, and other molecules. In some cases, collagen may refer to a group of naturally occurring proteins found in animals, for example, mammals. Natural collagen may form of elongated fibrils comprising a triple helix. In most cases the three helices of collagen comprise two identical alpha 1 chains ($\alpha$1) and one alpha 2 chain ($\alpha$2). In most cases collagen is post transcriptionally modified by hydroxylation, cross-linking, glycosylation, cleavage, etc. Collagen may be obtained from animals or animal cells. Collagen may be synthesized from a variety of cells include mammalian and non-mammalian cells such as bacteria using techniques well known to one of skill in the art. Proteoglycans may refer to proteins that are glycosylated. A proteoglycan may comprise one or more sulfated glycosaminoglycan (sGAG) chain(s) that may be attached at a Ser residue (generally in the sequence -Ser-Gly-X-Gly-, where X can be any amino acid residue). Proteoglycan chains are, in general, long, linear, and negatively charged under physiological conditions. Glycosaminoglycans can be assayed as a method of determining proteoglycan production from a cell using, for example, a dimethylmethylene blue colorimetric assay or enzyme-linked immunosorbent assay. In many cases, both the glycosaminoglycans in the micromass as well as the exchanged media (from media changes) are assayed. In some cases, discogenic cells grown in micromass culture in pro-chondrogenic media containing, for example TGF-B (transforming growth factor beta) or other growth factors known to produce a chondrogenic phenotype, may produce greater than about 1, 2, 3, 4, 5, 6, 7, 8, 9, 10 and less than about 20, 19, 18, 17, 16, 15, 14, 13, 12, 11 µg sGAG. In many cases, these results may be normalized to a quantification of cell number, DNA content or protein content, in order to determine proteoglycan production per cells. When normalized to cell number, the values may be greater than about 0.001, 0.005, 0.01, 0.02, 0.03, 0.04, 0.05, 0.06, and less than 1, 0.09, 0.08, 0.07 ng sGAG/cell. If the sGAG is normalized to its protein content, the values may be greater than 50, 60, 70, 80, 90, 100, 200, 300, 400 and less than about 1000, 900, 800, 700, 600, 500 ng sGAG/ug protein. In many cases, discogenic cells produce more or less soluble proteoglycan than other cells, for example fibroblasts, mesenchymal stem cells, or disc cells that may or may not have been grown in attachment-independent conditions grown for similar amounts of time.

Cells may be differentiated along adipogenic, osteogenic, and neurogenic lineages through techniques known to those skills in the art, such as the use of a StemPro multi-potentiality kit by Life Technologies, wherein specialized media is used to differentiated adherent monolayer cultures of cells. After osteogenic differentiation, presence of mineralized bone is identified with Alizarin Red dye. After adipogenic differentiation, presence of fat is identified with Oil Red O dye. After neuronic differentiation, presence of neuronal morphologies is observed. Additionally, genetic markers can be tested to identify relevant phenotypic changes.

Cells may be capable of self-renewal, which is defined as the ability to replicate without change to cell phenotype. This property can be identified in vitro via growth characterization over many passages, or in vivo through serial implantations and extractions.

In some embodiments, discogenic cells may produce extra-cellular matrix molecules. In other embodiments, discogenic cells may produce proteins. In other embodiments, discogenic cells may produce growth factors. In other embodiments, discogenic cells may produce cytokines. In other embodiments, discogenic cells may produce hormones. In other embodiments, discogenic cells may produce sugars.

After removal, reduction, or degradation of the extracellular matrix, cells from disc tissue may be transferred to either an attachment-dependent or attachment-independent culture system. In most cases, if disc tissue is submitted to an attachment dependent system, the receptacles may be treated with gelatin and/or collagen. In cases were the disc tissue cells are submitted to an attachment-independent culture system, the media may contain a viscous, non-reactive material to form a gel, such as methylcellulose.

Once attached, cells are passaged (detached from a vessel, resuspended at a lower density and again attached on a vessel) up to about 10 times. In some cases, the cells never reach confluence in the vessel. In other cases, the cells reach confluence in the vessel. Cells are passaged using standard cell culture techniques. When sufficient cell quantities are obtained, but prior to proliferative 'drop-off' (meaning that the cells divide at a significantly slower rate), the cells are transitioned to a suspension culture containing a viscous, non-reactive medium for the desired period of time. When complete, the cells are isolated, washed free of residual material, and further processed as needed for cryopreservation or direct therapeutic use.

Growth of disc tissue derived cells on gelatin or collagen-coated receptacles may allow growth, expansion, and/or differentiation of the discogenic cells. Discogenic cells can be added at 1,000-50,000 cells/cm$^2$. In these cases, cells may be grown in the presence of serum, EGF, and bFGF. In some cases, serum additives may added to the cell media, for example conditioned media from fibroblast cell cultures may also be added. In these cases, non-discogenic and less-discogenic cells may also grow, expand, and/or differentiate with the discogenic cells.

Growth of disc tissue-derived cells on in anchorage independent conditions may aid in the growth, expansion, and/or selection of discogenic cells. Discogenic cells can be added at 10,000 cells/mL or up to 80,000 cells/mL. In some cases, neuronal supplements, bFGF, and EGF may also be added to the attachment-independent cell culture media. In some cases, serum may or may not be added to the media. In most cases, disc cells from cultures of disc cells grown in attachment-dependent conditions produce less extracellular matrix than cells grown in attachment-independent conditions.

In most cases, the cells may be washed free of cell culture media. In some cases, the cells are washed with PBS, additional media, cryoprotectant media, etc. In some cases, the vessels are chilled at 4 C prior to washing to aid in dissolution of viscous components. Sometimes, repeated centrifugation is used to remove unwanted components. Sometimes, the cells are attached to a new vessel to allow for the removal of unwanted components. Sometimes, the cells are attached to carriers to allow for removal of unwanted components. Sometimes, chemical agents are used to remove unwanted components.

According to standard techniques, cells may or may not be detached from vessels or other cells using enzymes such as trypsin, recombinant trypsin, Accutase, HyQTase, TrypLE, etc. Cells may be combined with additional media and centrifuged at various speeds, including low speeds to allow for separation of different cell densities (single cells versus clusters), regular speeds to form a cell concentrate at the bottom, high speeds to form a tight cell pellet.

In many embodiments, a discogenic cell population is characterized by the ability to restore, regenerate, and/or grow disc tissue in vivo. For example, a discogenic cell population is able to restore damaged or diseased disc in a subject with a damaged or diseased disc. In many embodiments, the introduction of a discogenic cell population into a damaged disc of a subject will restore intervertebral disc height to about the pre-damage height.

Cell Morphology

Discogenic cells may be mononucleated. Discogenic cells may be multi-nucleated. Discogenic cells may contain organelles, such as mitochondria, Golgi apparatus, and ribosomes. Discogenic cells may be demonstrated to be viable according to trypan blue, alamar blue, live/dead assay (Life Technologies), or other assay. Discogenic cells may be capable of proliferating. Discogenic cells may be capable of producing extra-cellular matrix.

Discogenic cells grown under attachment-independent conditions may have a morphology that is different than discogenic cells grown as monolayers. For example, discogenic cells from attachment-independent cell culture may be isolated, rounded cells. Or, they may form cell clusters that are loosely associated with other cells and/or rounded cell associations. Or, they may form tight cell clusters known as Discospheres. Discogenic cell clusters may have at least one dimension that is greater than about 50 μm after sufficient growth. Discogenic cells may begin as isolated, rounded cells and over time, some cells may proliferate to form clusters or discospheres. This duration may be 1, 2, 3, 4, 5, 6, 7, 8, 10, 12, 14, 21, or 28 days. Discogenic cells may have associated extracellular matrix, such as proteoglycans and collagens.

Cell Population

In one embodiment of a discogenic population, the cells may include without limitation one or more of the following cells: a chondrocyte, a fibroblast, a nucleus pulposus cell, an annulus fibrosus cell, a mesenchymal stem cell, a stem cell, a progenitor cell, a cartilage cell. In another embodiment of a discogenic population, the cells may include without limitation one or more of the following cells having been modified ex vivo: a chondrocyte, a fibroblast, a nucleus pulposus cell, an annulus fibrosus cell, a mesenchymal stem cell, a stem cell, a progenitor cell, a cartilage cell. In another embodiment of a discogenic population, the population may include one or more of the following: isolated cells, or clusters of associated cells, or discospheres. In another embodiment of a discogenic population, cells may be separated to form an isolated cell population. In another embodiment of a discogenic population, cells may be aggregated to form at least one micromass. In another embodiment, the discogenic cells may be more therapeutic prior to separating the cells.

Therapeutic use of Discogenic Cell Populations

Discogenic cells may be delivered directly to a damaged tissue. Discogenic cells in an effective amount may or may not be combined with a biomaterial scaffold that is pharmaceutically acceptable to aid implantation. For example, a viscous natural material, containing hyaluronic acid, collagen or other extra-cellular matrix molecules, may be used. Or, a solid natural material may be used. In some cases, additives may be included for stability. In some cases, additives may be included to aid in cryopreservation.

It has been discovered in accordance with the present invention that damaged intervertebral discs can be repaired and/or the structure of the disc regenerated by administration of discogenic cells, thereby reversing or stabilizing degenerative disc disease and other disc injuries. It has also further been discovered that administration of such cells to a subject with an injured disc partially restored pre-injury disc height. Accordingly, the invention features methods for isolating and growing discogenic cells, for use in treating subjects having a disease of or damage to at least one intervertebral disc. In general, the methods comprise administering to the subject a therapeutically effective amount of discogenic cells such that repair and/or regeneration of the afflicted intervertebral disc(s) occur.

In highly preferred aspects, the methods comprise administering cells obtained or isolated from spinal column or other cartilaginous tissue to a subject in need of treatment for at least one diseased or damaged intervertebral disc, wherein the cells are capable of self-renewal and/or expansion in culture. Cells isolated from spinal column and cartilaginous tissue may be expanded or maintained in culture prior to administration.

In the presently disclosed methods, the discogenic cells can be administered in conjunction with biologically active agent(s). The discogenic cells can be administered in sequence with, or co-administered with the agents. Lysates, soluble cell fractions, membrane-enriched cell fractions, proteins, growth factors, hormones, cell culture media (e.g., conditioned media), or extracellular matrix derived from spinal, disc, or cartilaginous tissue or discogenic cells can also be administered to subject as appropriate, including co-administered discogenic cells themselves, and additional cells or agents. The particular agent chosen can be delivered as part of a kit from the provider. Or, the particular agent can be at the discretion of the medical professional directing the treatment of the subject, and can vary according to the particular needs or condition of the subject. The agent chosen can be used for various purposes such as, but not limited to, facilitating the administration of the cells, improving the repair and/or regeneration of the intervertebral disc, improving the overall health of the subject, reducing pain, and/or enhancing survival of transplanted cells.

The cells can be administered to the subject by injection. For example, the cells can be injected directly into one or more intervertebral discs of the subject. In many cases, the cells can be injected into the nucleus pulposus, transition zone, or annulus fibrosis of an intervertebral disc. The discogenic cells can be administered alone, or in combination with a biological or therapeutic, and/or scaffold or matrix agent(s).

In some embodiments discogenic cell populations may be implanted into a subject. For example, discogenic cell populations may be surgically implanted into a damaged or diseased disc. In some embodiments, a discogenic cell population may be surgically implanted into an intervertebral disc space where all or part of a disc has been removed. In some embodiments, a discogenic cell population may be implanted into an intervertebral disc space as part of an artificial or replacement disc.

The cells can also be administered as a scaffold- or matrix-cell complex. Scaffold and matrix compositions include but are not limited to proteins, hydrogels, synthetic polymers, and combinations thereof. Scaffold and matrix compositions may or may not be biodegradable. Such materials are known to one of skill in the art of therapeutic treatment, surgical repair, tissue engineering, and wound healing. Scaffold- and matrix-cell compositions can be introduced into a subject's body in any way known in the art, including but not limited to implantation, injection, surgical attachment, transplantation with other tissue, and the like. In some embodiments, the matrices form in vivo, or even more preferably in situ, for example in situ polymerizable gels can be used in accordance with the invention. Examples of such gels are known in the art.

The discogenic cells can be mixed with scaffolds and matrices prior to implantation or seeded onto such compositions in vitro, which may allow the cells to proliferate and/or establish extracellular matrix. In some cases, the matrix may resemble mammalian intervertebral disc structure, and the matrix may replace an entire intervertebral disc in a subject. In some cases, the matrices may include therapeutic agents.

The discogenic cells can be used to produce an artificial disc replacement device in vitro or in vivo. In one example, an appropriate non-resorbable material, such as polyurethane, is used to create an artificial outer annulus. In another example, a resorbable material, such as polygycolic or polylactic acid, is used. This artificial annulus serves as a container for discogenic cells, which may or may not be combined with at least one of the following—scaffold material, matrix material, carrier material, growth factor(s), and/or other biologically active agents. In many embodiments, the artificial annulus structure may be porous and/or fibrous. The artificial outer annulus may incorporate attachment means so that it can be fixed to one or more vertebral bodies. For example, the artificial annulus may incorporate through-holes, cuffs, tabs, loops, or washers to allow for screw fixation to one or more vertebral bodies. The artificial disc can be surgically implanted in a subject to completely replace a spinal disc.

Artificial disc replacement devices may comprise the disclosed discogenic cells. In various embodiments, discogenic cells may be inserted into an artificial annulus structure. The artificial annulus structure may be designed to provide a containment structure for the discogenic cells and may also further comprise attachment structures for securely attaching the disc replacement device to one or more vertebral bodies.

Discogenic cells are added to an artificial disc replacement device at or about the time of insertion of the disc replacement device. In other embodiments, discogenic cells are added to the disc replacement device well before insertion such that the cells can grow, divide, and provide a matrix or scaffold material. In many embodiments, scaffold material, matrix material, carrier material, growth factor(s), and/or other biologically active agents can be added to the disc replacement device before, after, or in combination with addition of discogenic cells to the disc replacement device.

Artificial disc replacement devices may comprise a resorbable or non-resorbable artificial annulus. In some embodiments, the artificial annulus may comprise matrix material, scaffolds, growth factors, or other biologically active agents to aid in supporting the growth of discogenic cells. In one embodiment, the artificial annulus supports the growth and/or differentiation of annulus fibrosus cells, for example by providing a localized source of growth factors and/or cytokines that may promote discogenic cell differentiation into annulus fibrosus cells. In many embodiments, the artificial disc replacement device comprising the discogenic cells may have a cellular architecture similar to that of a non-artificial intervertebral discs, for example comprising an annulus fibrosus, nucleus pulposus, and endplate tissue.

In some cases, discogenic cells and scaffold may be cryopreserved in liquid nitrogen. Or, they may be stored at various sub-zero temperatures, such as −80 C, −20 C, or −1 C. Additionally, the discogenic cells may be stored at 4° C. or 37° C. The discogenic cells may be combined with a scaffold prior to storage. Or, the discogenic cells may or may not be combined with a scaffold immediately prior to implantation.

A successful treatment could thus comprise treatment of a subject with a disease, pathology, or trauma to the intervertebral disc with a therapeutic cell composition comprising the discogenic cells, in the presence or absence of therapeutic agents, matrices, or scaffolds. The cells are present in an effective amount to promote, for example, direct proteoglycan production or stimulation of native cells to regenerate. The result could be regeneration, repair, or reconstruction of native tissue architecture, as shown in a rabbit model. This can be determined via medical imaging (x-ray, MRI) or reduction in pain. In the case of implantation into a human intervertebral disc, cell content can be 1,000-10,000,000, containing a discogenic cell population or a subpopulation extracted from discogenic cells. The scaffold volume can also range, from 10 μL to 1000 μL, or 10 mg to 10 g, depending on the spatial needs of the subject.

In some embodiments, one or more subpopulations of cells within discogenic cells may be implanted. This subpopulation may be isolated using magnetic beads for sorting, fluorescent markers for sorting, density gradients, fluorescent genetic tagging for sorting, physical separation, filtration, etc. This subpopulation may be additionally therapeutic compared to the entire population.

Upon treatment of a subject, discogenic cells may provide superior therapeutic effect compared to attachment-dependent discogenic cells or other cell populations, such as nucleus pulpous cells, fibroblasts, chondrocytes, stem cells, progenitor cells, etc. This effect may or may not be improved through the use of scaffolds, carriers or other biomaterials.

Also featured in accordance with the present invention are kits for practicing the disclosed methods. In one aspect, kits for treating a subject having a disease of or damage to at least one intervertebral disc are provided. The kits may comprise a pharmaceutically acceptable carrier, discogenic cells in an amount effective to treat the disease or injury, and instructions for using the kit in a method for treating a subject having a disease of or damage to at least one intervertebral disc. The kits may further comprise at least one reagent and instructions for culturing the cells. The kits may further comprise at least one biologically or therapeutically active agent. The kits may further comprise vials and syringes. The kits may further comprise discogram needles for direct entry into the intervertebral disc. The kits may further comprise a radiopaque agent to aid in imaging during the procedure.

Experimental Details Section

Materials and Methods
Supplies/Reagents:

In some cases, attachment dependent cell culture may be referred to as Expansion Conditions. Expansion Medium may be used for growth of cells under Expansion conditions. Expansion medium contained DMEM/F12 with 10% fetal bovine serum. 30% of this medium can be optionally pre-conditioned in the presence of neonatal foreskin fibroblasts for 3 days. This pre-conditioned portion was filtered prior to use. Prior to adding Expansion Medium to cells, bFGF and EGF are added to make the media 'complete' with final concentrations of 10 ng/mL bFGF and 10 ng/mL EGF, obtained from stored 1000× stock solutions.

In some cases, attachment independent cell culture may be referred to as Suspension Conditions. Suspension Medium may be used for growth of cells under Suspension conditions. Suspension medium contained 1% A4M Premium methylcellulose (Dow Chemical) in DMEM/F12 supplemented with 1× B27 (Life Technologies), 5% fetal bovine serum, 10 ng/ml EGF, and 10 ng/ml bFGF. Suspension feeding medium is the same, minus the methylcellulose.

For expansion, Plates or Flasks coated with collagen, gelatin or another similar matrix protein were used. These vessels were purchased pre-made. Or, plates can be coated manually by dissolving 1 g powdered gelatin (Sigma) in 1 L ddH20 (double distilled water) or prepared from premade solutions (Sigma) by diluting the solution to 1% final concentration. If coating in the lab, the receptacles are then incubated at room temperature for 15 minutes or more. For suspension, ultra-low attachment vessels were used from Corning.

In some cases, a viscous scaffold carrier was used to implant the cells in vivo. Specifically, a pre-manufactured sterile gel composed of 1.7% hyaluronic acid (0.8-1.2 MDa) in PBS was diluted with human serum albumin and 30,000 discogenic cells to result in a 1% hyaluronic acid gel with 2.5% human serum albumin. This was loaded into sterile 50 ul glass Hamilton syringes. 27 gauge Precision Glide needles were fixed onto the Hamilton syringes via leur-lock for animal implantation.

Methods:

Human adult nucleus pulposus tissue is obtained from consenting surgical donors using an IRB-approved protocol. In various embodiments, tissue may be obtained from a variety of sources and tissues, for example, living and deceased non-autologous donors, autologous donors, intervertebral tissue, or from other cartilaginous tissue. Non-nucleus pulposus tissue, including annulus fibrosis and cartilaginous endplate, was manually resected and discarded. 2-7 grams of the resulting tissue was combined with 15 ml DMEM/F12 containing 300 units/ml of collagenase II in a T75 flask, and incubated overnight under standard tissue culture conditions (37° C. and 5% $CO_2$). Next, the liberated cells were transferred into a 50 ml tube, the cells spun down (4 min, 1200 rpm), supernatant removed and the cells resuspended in DMEM/F12 to a final concentration of about 10,000 cells/ml.

Alternatively, cells were obtained from cryopreserved vial (stored in liquid nitrogen) by thawing in 37 C water bath and immediately transferring to a 15 mL tube containing 10 mL of expansion medium. The cell mixture was then centrifuged for 4 minutes at 1200 rpm. The supernatant was then aspirated and the cells resuspended in expansion medium to count cells and confirm viability.

For expansion, cells were plated at 10,000 cells/mL in complete expansion medium, and the medium replaced every 2-3 days. Prior to confluence, cells are washed with PBS, incubated with 0.25% trypsin for 7 minutes, and then removed from the plate with expansion medium and transferred into a 50 ml conical tube. The tube was spun as previously described, and the supernatant containing trypsin was removed. The cells were then resuspended in expansion medium to allow for cell counting and viability check. At this point, cells could be cryopreserved by combining 0.5-3 million cells with 90% FBS/10% DMSO in a cryovial. To freeze the contents, the cryovial was stored overnight in −80 and then moved to vapor phase of liquid nitrogen for long-term storage.

For suspension culture, the cells were combined with suspension medium at 10,000 cells/ml (15 ml total) and added to ultra-low attachment 100 mm dishes (Corning). Every 2 days, 300 μl of suspension feeding medium was added to the dish. Images were captured at 4×, 10× and 20× using a phase-contrast light microscope, as in FIG. 2. After 2 weeks, the cells were harvested by incubating the plates at 4° C. for 20 minutes, followed by diluting the gel-like medium with 15 mL PBS. The contents of the plate were then transferred to a 15 mL tube, the volume increased to 50 mL with additional PBS, and spun at 1200 rpm for 4 minutes, and the supernatant removed. The cells were then washed twice more in this manner, to ensure removal of methylcellulose. Finally, the discogenic cells were resuspended in expansion medium to allow for cell count and viability check.

To determine surface marker expression, the discogenic cells are combined with 0.25% trypsin for 7 minutes to create a single-cell suspension. Additional cell populations tested included: pre-discogenic cells from expansion culture, adult human mesenchymal stem cells (CET Company), human neonatal foreskin fibroblasts (AATC), and human adult articular chondrocytes (ScienCell). The cells were analyzed using standard techniques with a Partec Cyflow flow cytometer. Briefly, 70,000 cells and antibodies (one type per tube) were diluted in 200 ul PBS containing 0.5% bovine serum albumin and incubated for 30 minutes at 4 C in dark conditions. The following antibodies were used: CD73-PE (BD), CD90-PE-Cy5 (BD), CD105-PE (Miltenyi), CD166-PE (BD), HLA-ABC (BD) and control. The work was performed in duplicate, with one representative data set shown.

To determine proteoglycan production in a pro-chondrogenic environment, a standard chondrogenic pellet assay was utilized. Briefly, 200,000 cells (discogenic cells or mesenchymal stem cells) were added to individual conical wells in a 96-well plate with 200 µl pro-chondrogenic media (StemPro media, Life Technologies) and spun briefly in a centrifuge. Every 3 days, the media was removed, collected and replaced, taking care not to aspirate the central micromass that formed. After 2 weeks (see FIG. 3), the cell pellets were harvested, dried and digested overnight in 250 ul of papain (Sigma) in a buffer at 60 C. The digestate, along with the collected media, was assay for sGAG content, a component of proteoglycan, using a standard DMMB assay. Specifically, to make the DMMB working solution, 1 g of sodium formate was dissolved in 490 mL of deionized water and 1 mL of formic acid was added. In another tube dissolve, 8 mg of dimethylmethylene blue (DMMB) powder (Sigma) was combined with 2.5 mL of ethanol, and the two solutions were combined. Then, water was added to bring the volume up to 500 mL. To make the chondroitin-6-sulfate standards, 40 mg of chondroitin-6-sulfate (C6S) was mixed with 40 mL of water to make 1 mg/mL of standard solution (stock). Then, the stock was diluted to make 0, 1.0, 2.0, 3.0, 4.0, 5.0, 6.0, 7.0, 8.0, 9.0, 10.0 µg/mL. To assay for proteoglycan content, 100 ul of standards or sample and 100 ul of DMMB working solution was combined in a 96-well clear plate and read within 5 minutes at 525 nm. The standards were used to determine a concentration of the sample, and then the concentraton was normalized to original volume to determine mass. Additionally, the digestate was assayed for protein content using the Pierce protein assay per manufacturer instructions, or DNA content using the Quanti-IT PicoGreen Assay (Life Technologies) per manufacturer instructions.

To determine Osteogenic and Adipogenic potential (FIG. 4), discogenic cells were grown using the StemPro Osteogenic and Adipogenic Kits (Life Technologies) according to the manufacturers instructions.

To assess in vivo efficacy, 30,000 discogenic cells were combined with 25 ul of 1% hyaluronic acid (0.8-1.2M Da) in PBS containing 2.5% human serum albumin. The cell and viscous scaffold were loaded into 50 ul glass Hamilton syringes. Using a previously internally validated model of degenerative disc disease, lumbar discs of 3 New Zealand rabbits were accessed surgically and punctured with a needle to induce degeneration (n=4 discs/animal, approved by local IACUC). After two weeks, either cell therapy or a cell-free scaffold control was injected into the injured discs. Additionally, injured and uninjured control lumbar discs were maintained in each animal. Every 2 week for 6 weeks, disc height was measured using plain radiographs and normalized to week 0 values, resulting in a Disc Height Index (DHI). After 6 weeks, the rabbits were euthanized; the discs were harvested and prepared for histology. Sections were stained with H&E or Alcian blue, and blindly scored for abnormality, assigning a score of 0 to 2 for AF/NP border, AF organization, NP extra-cellular matrix, and NP cellularity (AF—annulus fibrosus; NP—nucleus pulposus) and summing the 4 results (0—normal, 8—abnormal).

EXAMPLES

The following examples describe in detail the preparation and properties of embodiments of the microenvironments of the present disclosure. It will be apparent to those skilled in the art that many modifications, both to configurations, materials, and methods, may be practiced without departing from the scope of the disclosure.

Example 1

Surface Marker Expression of Various Cell Types Via FACs Analysis

Cell surface marker expression was analyzed for a variety of cells including discogenic cells. As shown in FIG. 1, Human cell types tested include adult mesenchymal stem cells, neonatal foreskin fibroblasts (Fibro.), articular chondrocytes (Chondro.), anchorage-dependent discogenic cells (AD-DC), anchorage-independent discogenic cells (AI-DC). FIG. 1A shows the percent of cells expressing given marker based on standard IgG gating. DC cells show lowered expression of CD105 and CD166 compared to other cell types. Other surface markers are being explored to identify unique a unique phenotypic fingerprint for DCs. FIG. 1B presents representative flow cytometry analysis of cell markers in MSCs, pre-discogenic cells and discogenic cells for CD105 and CD166 showed unique pattern of discogenic cells.

Example 2

Morphology of Discogenic Cells in Suspension Culture

Figure 2A:
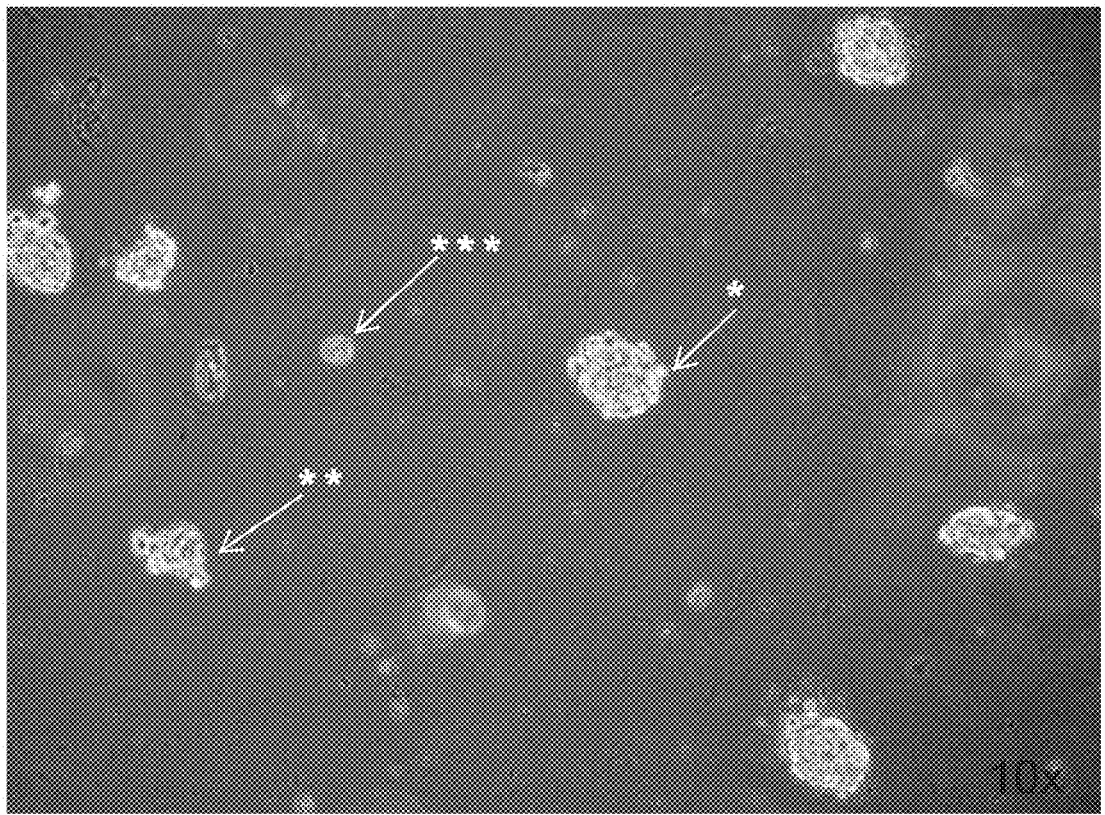
FIGS. 2A-B show cell morphology of discogenic cells grown in suspension culture.
Figure 2B:
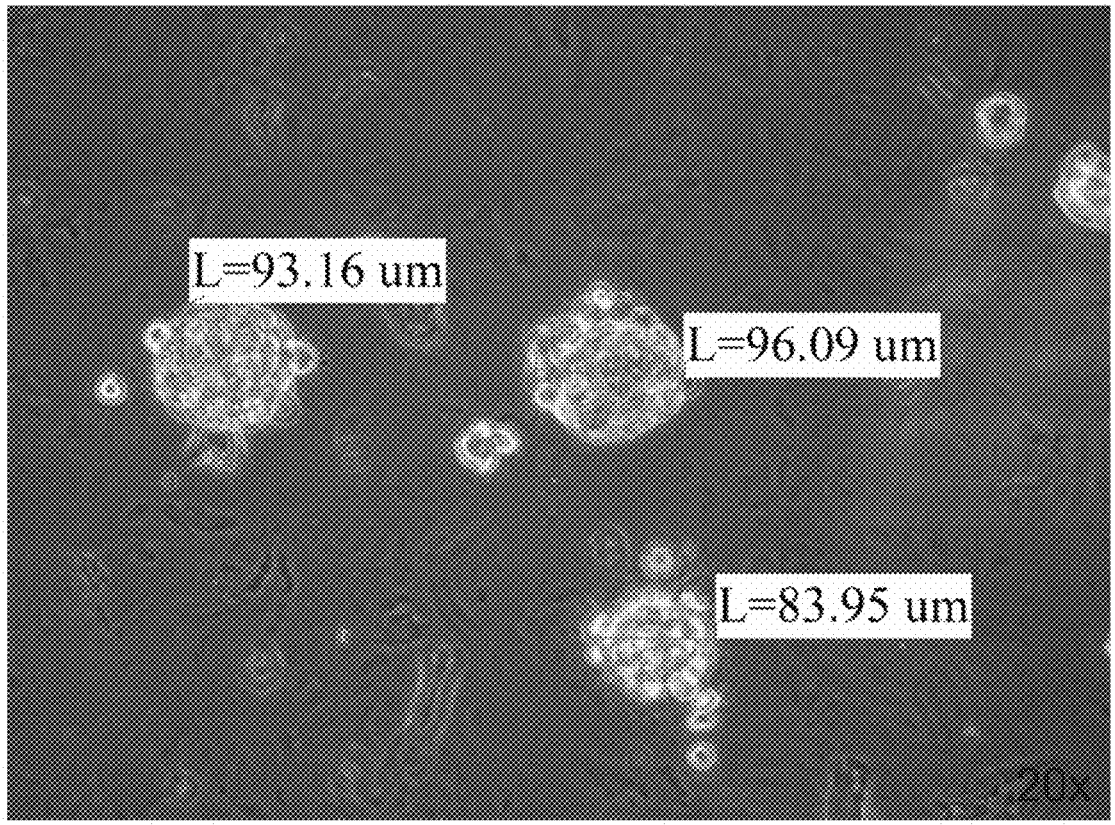

The morphology of discogenic cells was investigated. FIG. 2A is a micrograph showing discogenic cells consist of tight spheroids known as discospheres (*), loose aggregates of cells (), and single cells (*). FIG. 2B shows that discosphere and aggregate diameters vary, and are typically larger than 50 um.

Example 3

Chondrogenic Potential of Mesenchymal Stem Cells (MSCs) and Discogenic Cells (DCs)

Figure 3A:
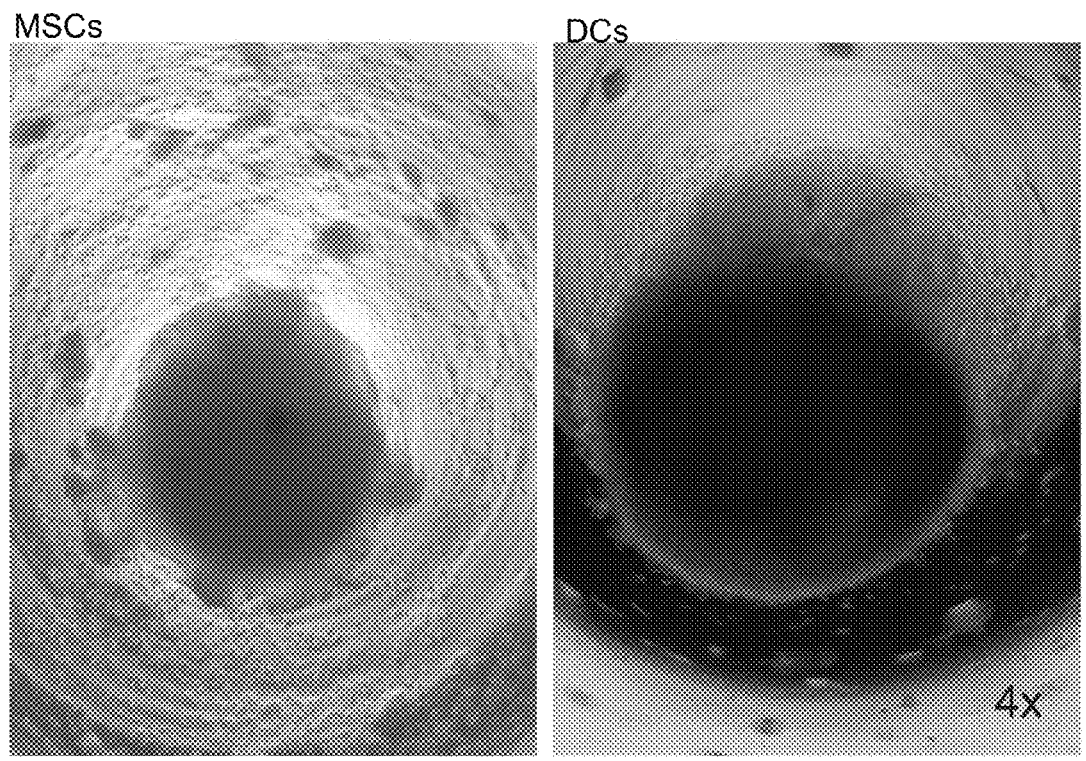
FIGS. 3A-B show the chondrogenic potential of discogenic cells compared to MSCs.
Figure 3B:
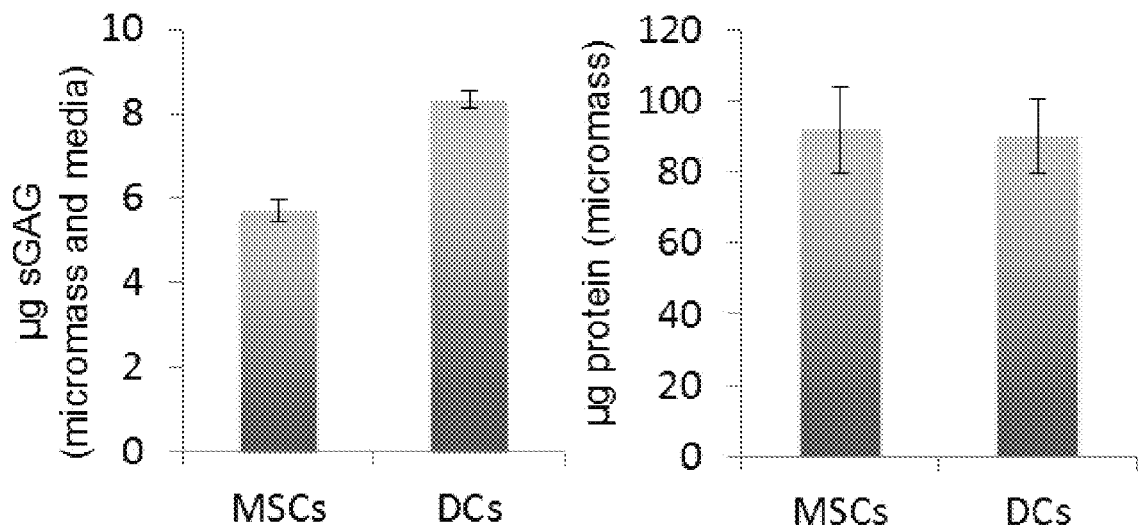

FIG. 3 shows analysis of chondrogenic potential of mesenchymal stem cells and discogenic cells. FIG. 3A shows morphology of cells after 2 weeks of growth in pro-chondrogenic environment, as shown here, the DCs produce larger micromasses than the MSCs. FIG. 3B are graphs comparing MSC and DC production of protein and GAGs. As shown here, DC produced more sGAG (a component of proteoglycan), collected from both the media and digested micromass, compared to MSCs, despite comparable protein content in each micromass.

Example 4

Adipogenic and Osteogenic Potential of Discogenic Cell Population

FIG. 4A shows that adipogenesis was confirmed via Oil Red O staining counterstained with hematoxylin after differentiation in adipogenic media using manufacturer's instructions (Life Technologies). FIG. 4B shows that osteogenesis was confirmed via Alizarin Red staining after differentiation in osteogenic media using manufacturer's instructions (LifeTechnologies). (Scale=50 μm)

Example 5

Discogenic Cell Viability at Various Stages Prior to Therapeutic Use, Via Live/Dead Assay (Green Indicates Live, Read Indicates Dead)

Figure 5A:
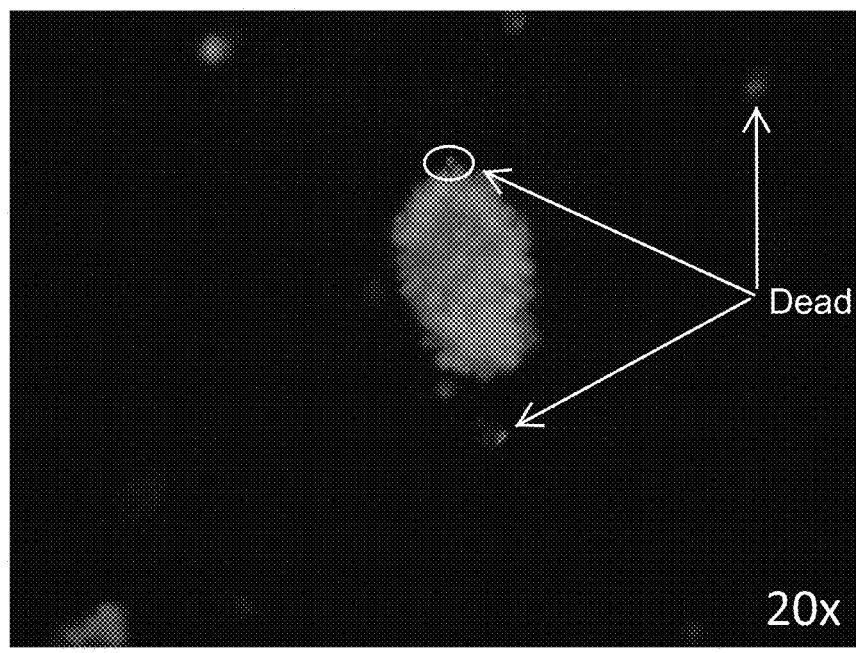
FIGS. 5A-B show the viability of cells (green, or bright in B/W—alive, red or dark in B/W— dead) after being combined with a viscous 1% hyaluronic acid scaffold, and after being extruded through a 27-gauge 1.5 inch surgical needle.
Figure 5B:
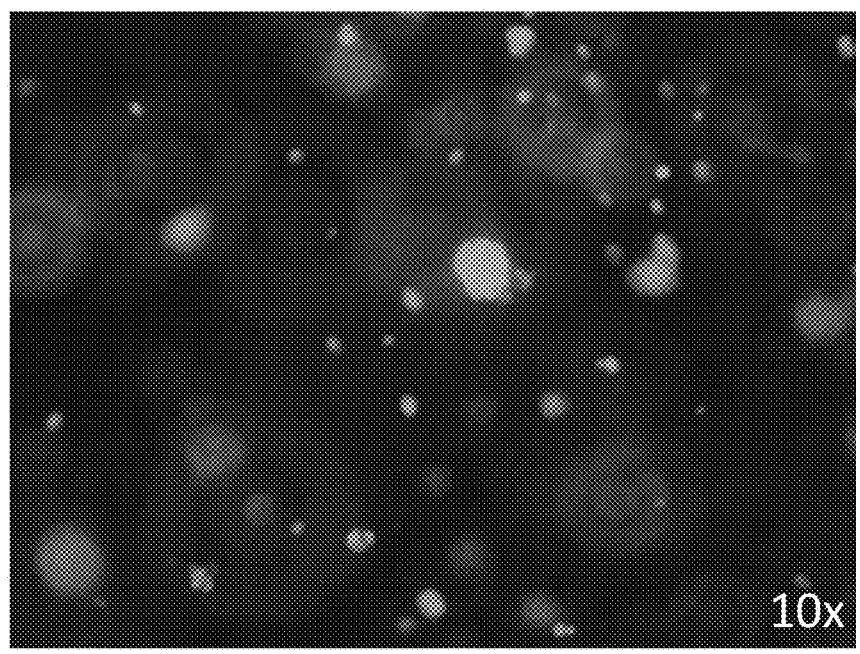

FIG. 5A shows that viability is confirmed after 24 hours in viscous hyaluronic acid scaffold, where the majority of cells are alive (bright cells; some dead cells are indicated with arrows). FIG. 5B shows that viability (bright cells) is again confirmed after being extruded through 27 gauge surgical needle used for surgical implantation into rabbits.

Example 6

Therapeutic Use of Discogenic Cells with a Viscous Scaffold Carrier

Figure 6A:
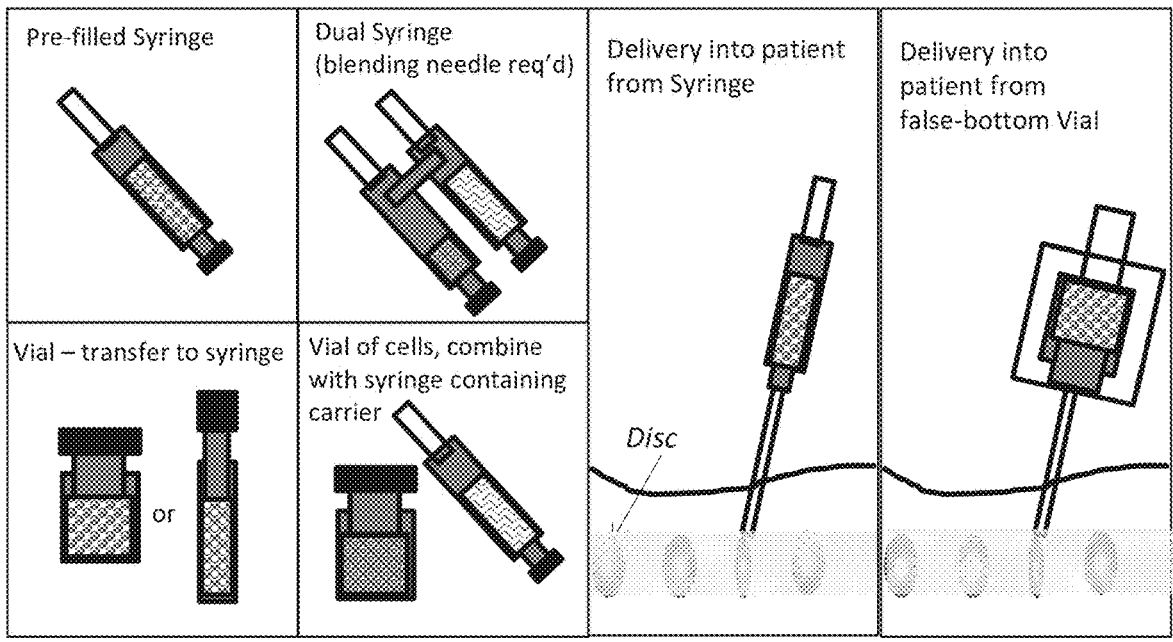
FIGS. 6A-B show potential devices and formulations for the therapeutic use of discogenic cells to treat various forms of disc disease. Treatment can be by injection (top) or implantation (bottom). Cells and carrier/scaffold can be together, or combined immediately prior to use.
Figure 6B:
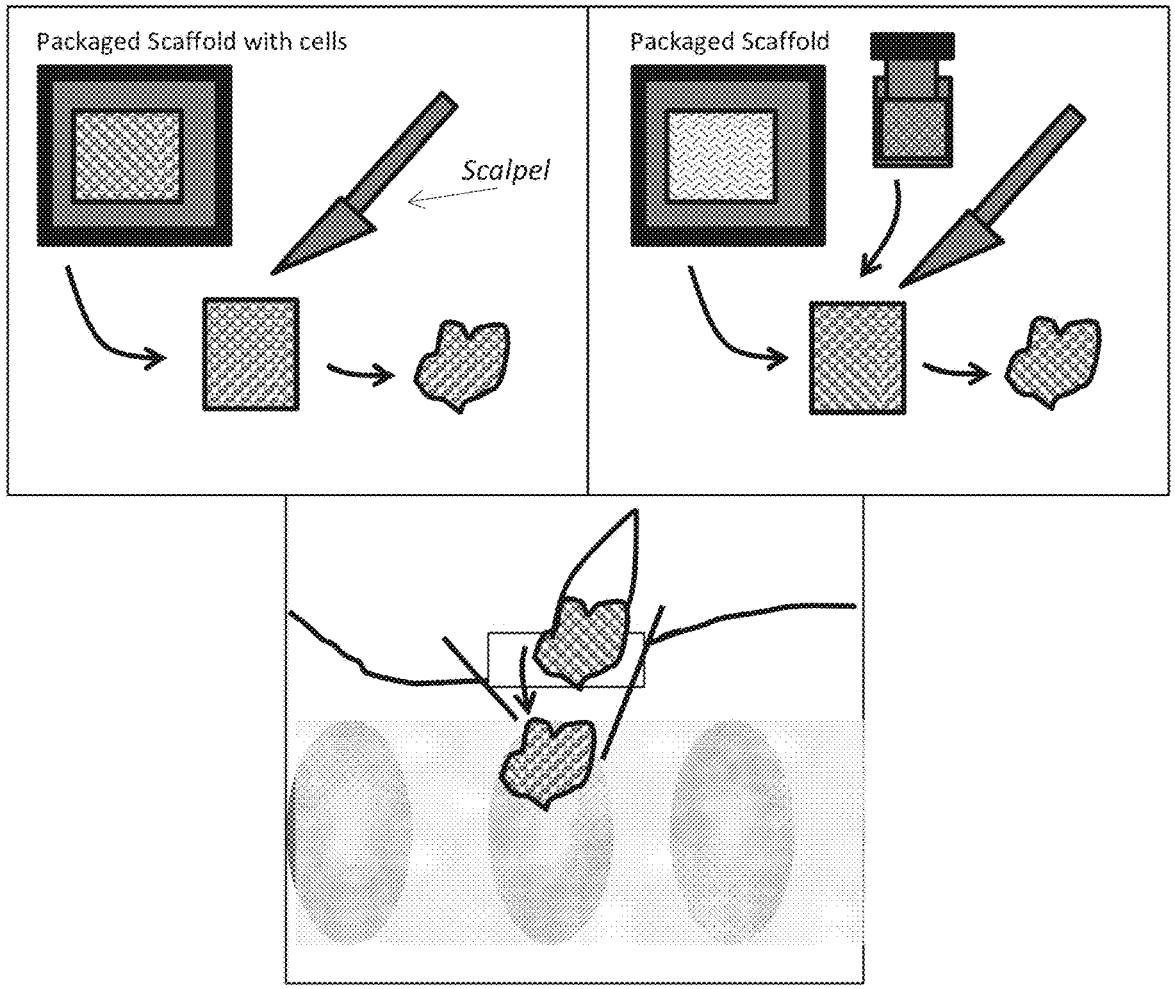

FIG. 6 is a schematic diagram showing embodiments and steps of using discogenic cells to treat DDD. FIG. 6(A) I depicts the use of discogenic cells by injection. Cells and scaffold may be mixed and pre-filled into a syringe or vial. Cells and scaffold may be separate and mixed immediately prior to injection. Product can be delivered from a syringe or false-bottom vial. Product is injected directly into a degenerated disc. (B) FIG. 6B depicts discogenic cell implantation. Cells and scaffold may be combined, or delivered separately. Prior to implantation, the material is cut or modified to fill the intended implantation area. The material is then implanted into the defect. The cells may be added after implantation (not shown). For the in vivo animal study presented, cells and scaffold were mixed and shipped at 4° C. in a vial, and the contents loaded immediately prior to injection into a syringe.

Example 7

Figure 7A:
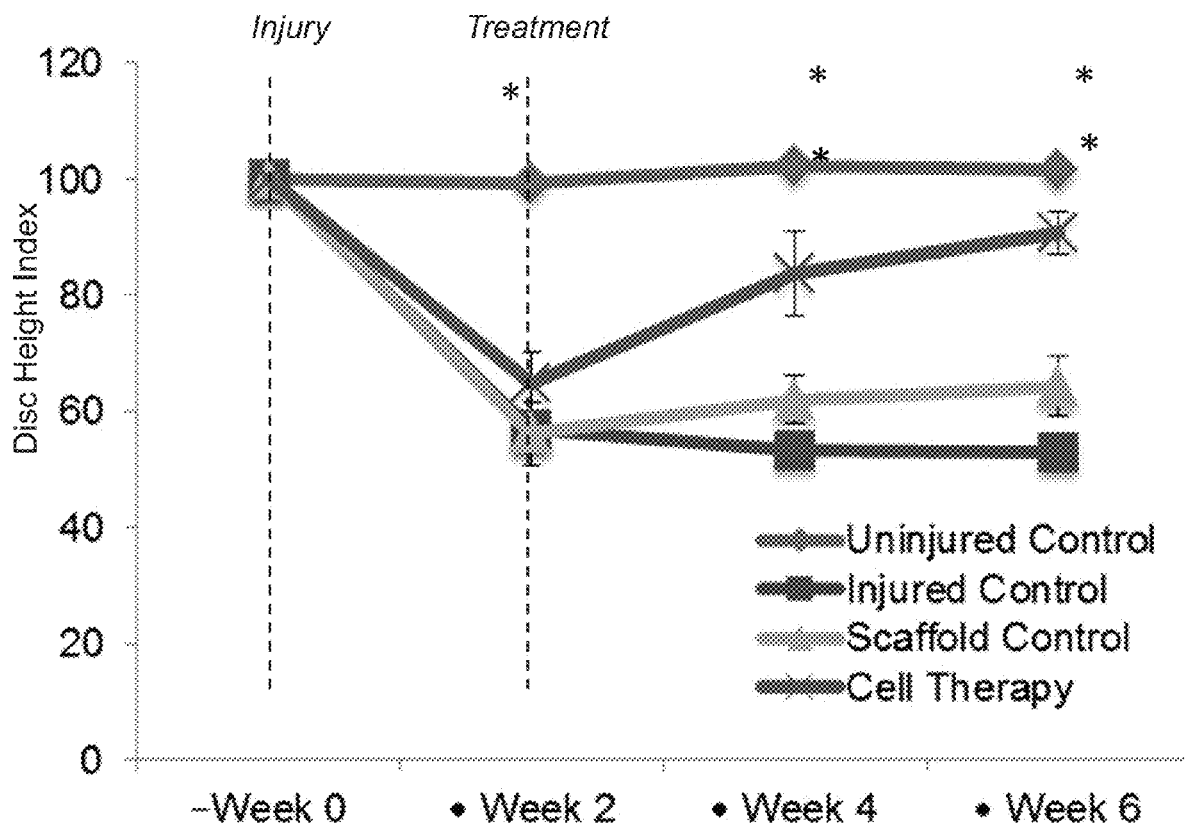
FIGS. 7A-B show the in vivo efficacy to repair degenerated intervertebral discs (animal model) of discogenic cells formulated with a viscous scaffold carrier in rabbits.
Figure 7B:
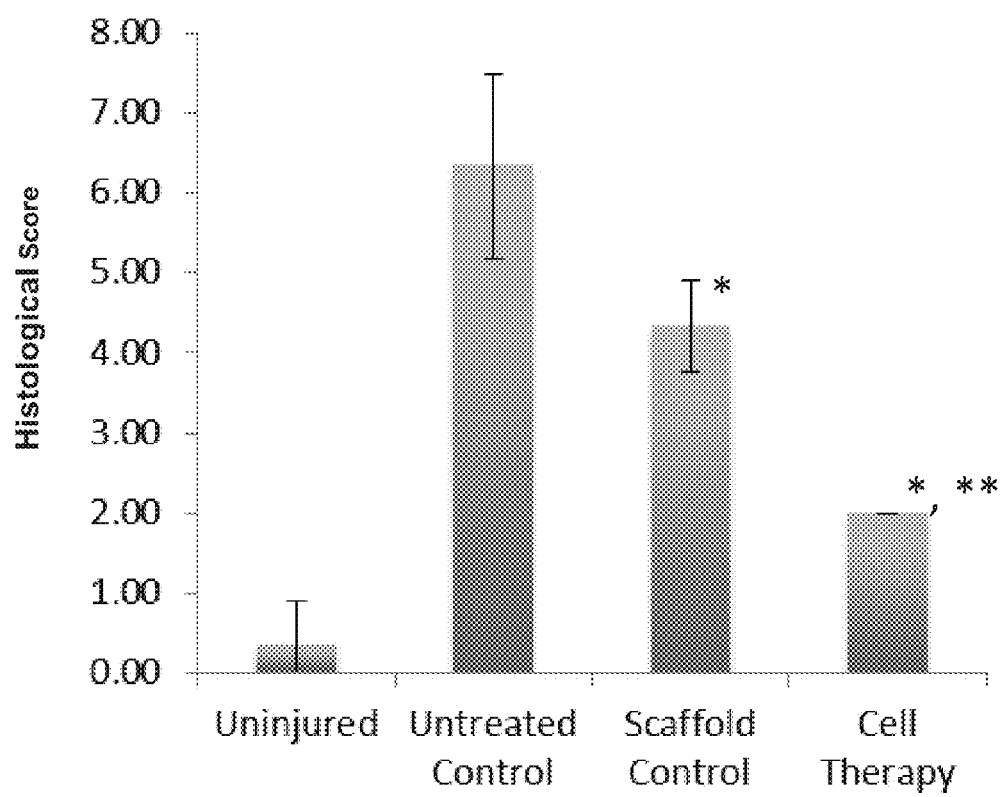

Efficacy of Discogenic Cells in a Viscous Scaffold Carrier in a Rabbit Model of Degenerative Disc Disease FIG. 7A is a graph showing that discogenic cell therapy within a scaffold carrier restored disc height index (DHI) compared to control groups at 4 and 6 weeks. All control groups were consistent between week 2, 4 and 6. N=3, * indicates p<0.001 compared to both Scaffold Control and Injured Control using 2-way ANOVA and Tukey's Post-hoc test. FIG. 7B is a graph showing the histological score. Blind scoring of discs at week 6 (0-8, 0=normal). The cell therapy showed significant improvement compared to injured control and scaffold control. ** indicates p<0.05 compared to scaffold control, * indicates p<0.05 compared to injured control, using t-test.

Example 8

Production and Assessment of Discogenic Cells

Materials and Methods
Production of Discogenic Cells

The described procedure is depicted in the flow diagram in FIG. 8. First, discarded adult human nucleus pulposus tissue from discectomy procedures was procured with IRB from consenting donors (Baptist Hospital, TN). Fibrous, annulus material and other tissue contaminants were removed via dissection. The remaining material was then washed three times with 2× antibiotic-antimycotic (ABAM, HyClone by Thermo Scientific) in PBS, and digested overnight in 300 units recombinant type-2 collagenase (Life Technologies) in DMEM/F12 (Life Technologies) with 1×ABAM. The isolated cells were plated onto gelatin-coated flasks in expansion medium (DMEM/F12 with 10% FBS by Hyclone, 10 ng/mL EGF and 10 ng/mL FGF-2 by Pepro-tech), and over time a subpopulation of cells attached to the plates, composed of stem/progenitor cells. These cells were expanded for up to 4 passages.

Next, the cells were combined with suspension medium (10,000 cells/cm2 in DMEM/F12 with 5% FBS, 10 ng/mL EGF and 10 ng/mL FGF-2) in the presence of 1% methylcellulose (A4M Premium, Dow Chemical), adding 1.5 mL of media per cm2 in ultra-low attachment vessels (Corning; Corning, NY). After 2 weeks, the cells were harvested from methylcellulose for further use with 3 washes in phosphate buffered saline (PBS, Corning CellGro; Manannas VA Discogenic cells were produced from 5 distinct human don A suspension of discogenic cells was fixed in 10% formalin (Sigma-Aldrich; St. Louis, MO) for 15 minutes.

Histology of Discogenic Cells

Next, the cells were washed with PBS 3 times and cells resuspended in 37° C. agarose (approximately 1×107 cells per 0.5 mL in 1% BioReagent low gelling temperature agarose by Sigma). When the agarose solidified, the pellet was kept in PBS until frozen in OCT medium (Sakura Tissue-Tek; Torrance, CA) in a Leica Cryostat and sectioned 6 μm thick onto charged slides. Samples were then stained with either hematoxylin and eosin, alcian blue counterstained with nuclear fast red, or picrosirius red, according to standard protocols. Histology shown is from one representative donor.

Confocal Microscopy

A suspension of discogenic cells was fixed for 15 minutes in 10% formalin and washed 3 times in PBST (PBS+0.1% Triton 100× by Sigma; St. Louis MO). Subsequently, primary antibodies in PBSTA (PBST+0.5% human albumin by Baxter Healthcare; Westlake Village CA) were diluted 1:100 for anti-human aggrecan (Santa Cruz Biotechnology; Dallas TX) and 1:20 for anti-collagen II (Developmental Studies Hybridoma Bank; Iowa City, Iowa) with fixed cells and incubated for 2 hours at room temp followed by 3 washes in PBST. The cells were then conjugated with Alexa-Fluor 488 for aggrecan and 633 for Collagen II in (both in PBSTA) for 1 hour at room temp and washed again 3 times with PBST. Finally, cells were then counterstained with DAPI and Phalloidin (Molecular Probes by Life Technologies) for cell nuclei and actin, respectively, and imaged using an Olympus FV 1000 confocal microscope. Histology shown is from one representative donor.

Flow Cytometry

Cell surface antigen expression of discogenic cells were analyzed by flow cytometry using the following fluorescence-conjugated mouse anti-human monoclonal antibodies: CD105-phycoerythrin (PE, Miltenyi Biotec, Inc., Auburn, CA, USA); Stro-1-Alexa Fluor 647 (BioLegend, San Diego, CA, USA); CD166-PE, CD73-APC, and CD90-FITC, CD44-FITC, CD-24-PerCP-Cy5.5, CD34-PE, HLA-DRDP-FITC, HLA-ABC-FITC (all from BD Biosciences, San Jose, CA, USA). Appropriate isotype controls were run in parallel. The cells were incubated for 30 minutes at 4oC in PBS containing 50% mouse serum and subsequently washed and resuspended in PBS containing 1.0% bovine serum albumen. DAPI, dilactate (Life Technologies, Carlsbad, CA, USA) was used to assess viable cell content. A minimum of 20,000 events were collected on a FACSCanto flow cytometer (BD Biosciences, San Jose, CA, USA) using FlowJo Software for data acquisition and analysis.

Multipotentiality

Osteogenesis and adipogenesis was induced using kits supplied by Life Technologies (Grand Island, NY). Briefly, discogenic cells were dissociated for 15 minutes using TrypLE (Gibco by Life Technologies) to form a single-cell suspension and plated onto tissue-culture treated dishes at 20,000 cells/cm2. Dishes of cells for osteogenic and adipogenic differentiation were maintained in DMEM with 10% FBS for 3 days, and then fed with the appropriate supplied differentiation media for 3 weeks. After differentiation, the monolayers were stained for calcification with Alizarin red or lipid content with Oil Red O as instructed. Phase images were captured at various magnifications. The study was performed on 4 distinct donors.

Chondrogenesis was induced as described in [Johnstone 1998]. Briefly, 250,000 cells were added to individual conical wells in a 96-well plate with 200 µl chondrogenic media (Life Technologies) and spun briefly. Every 3 days, the media was completely removed, collected and replaced, taking care not to aspirate the central micromass that formed. After 2 weeks, the cell micromasses were harvested, dried and digested overnight in 250 ul of papain (Sigma-Aldrich) at 60° C. The digestate, along with the collected media, was assay for GAG content as in [Farnesdale]. Additionally, the digestate was assayed for DNA content using the Quant-IT PicoGreen Assay (Invitrogen), and the results normalized to assess GAG/DNA.

For comparison, the chondrogenic potential of discogenic cells was assessed with other, well-known adult human cell lines. Articular chondrocytes (Sciencell; Carlsbad, CA), bone-marrow derived mesenchymal stem cells (CET by Thermo Scientific; Waltham, MA), and dermal fibroblasts (ATCC; Manassas VA) were purchased and expanded according to provided instructions.ors.

Results

Histology, Confocal Microscopy and Gene Expression

The discogenic cells were assayed for aggrecan and collagen production. After 2 weeks in non-plastic adherent culture, individual NP-derived stem/progenitor cells proliferated into clusters of various sizes embedded in extracellular matrix (ECM). The matrix was composed of proteoglycan and various collagens (FIG. 9A-C), the main components of nucleus pulposus tissue. Confocal imaging was used to identify aggrecan and collagen 2 in the ECM, with variability in matrix content noted across clusters (FIG. 9D). Further, high-magnification imaging revealed both intra- and extra-cellular aggrecan (FIG. 9E), suggesting active transport of ECM molecules out of the cell at the time of imaging.

As depicted in FIG. 9F, the expression of aggrecan and collagen 2 was assessed over time in culture (day 3 and 7), at cell harvest (day 14) and after chondrogenic differentiation compared to the housekeeping gene HPRT. During the course of the culture period, expression of the extracellular matrix molecules increased significantly, with approximately 20-fold more expression of aggrecan and 70-fold more expression collagen 2 compared to the plastic-adherent cells. Gene expression was further upregulated upon chondrogenic differentiation.

Flow Cytometry

Figure 10A:
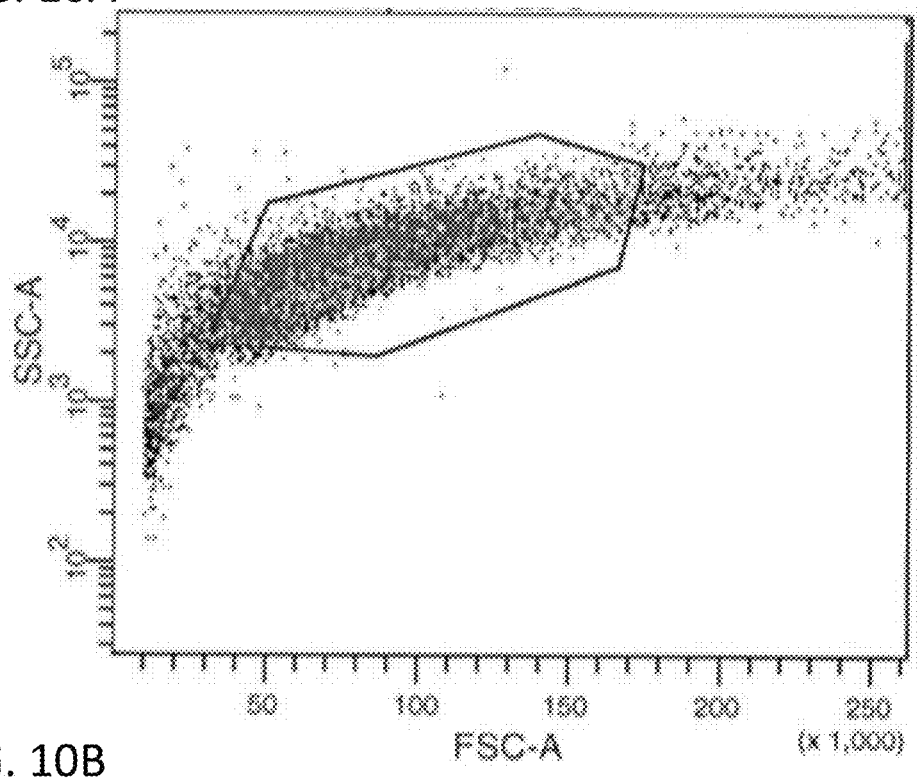
FIGS. 10A-C depicts flow cytometry studies on discogenic cells.
Figure 10B:
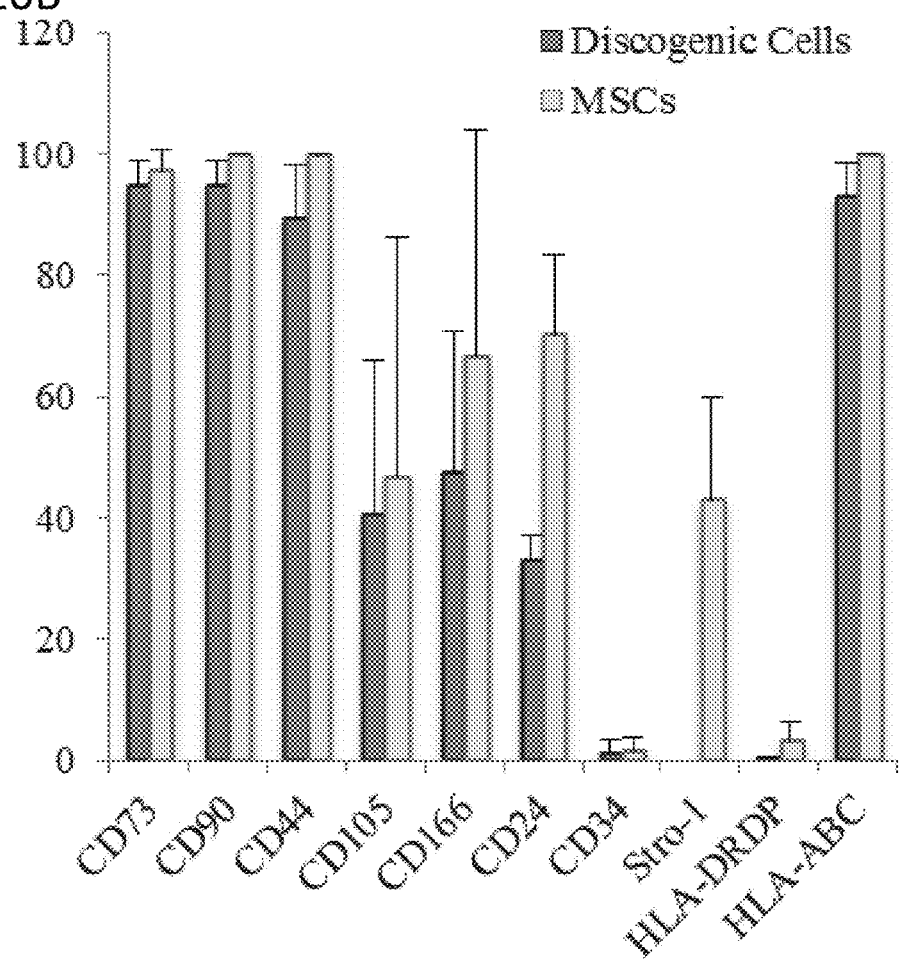
Figure 10C:
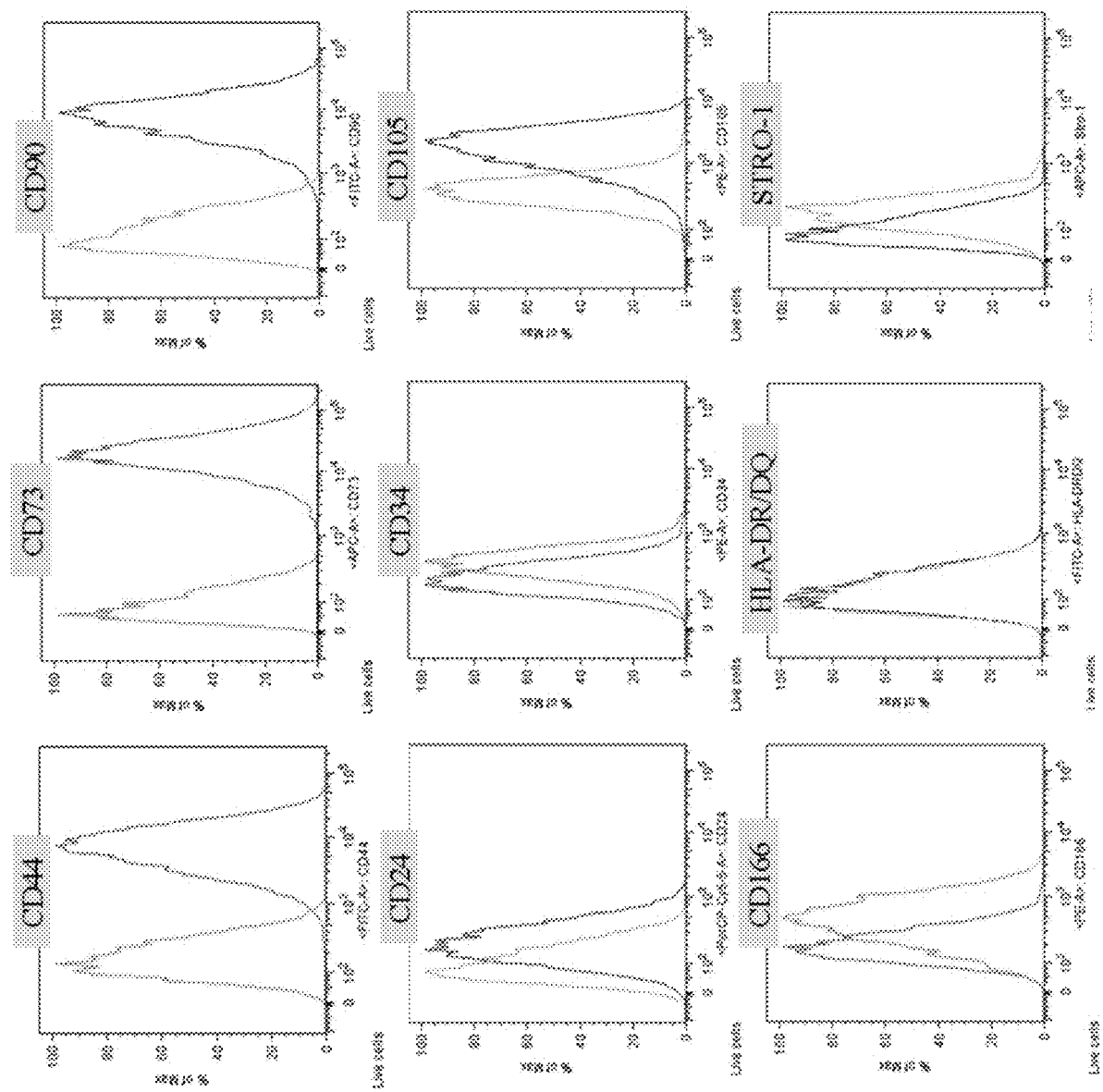

Discogenic cells were dissociated to form a single-cell suspension, and analyzed for various surface markers using flow cytometry. The population was homogenous in terms of size and internal structure, as seen in the forward/side scatter plot shown in FIG. 10A). A broad range of surface markers were tested and compared to mesenchymal stem cells (as a control). The expression of these markers was generally uniform across 5 distinct human donors (p>0.05) with >80% expression of CD44, CD73, CD90, HLA-ABC, and <10% expression of CD34, HLA-DR/DQ and STRO-1 compared to isotype controls (FIGS. 10B and 10C). CD24, CD105 and CD166 were expressed at approximately 40%, with slightly more variability.

Multipotency

Figure 11A:
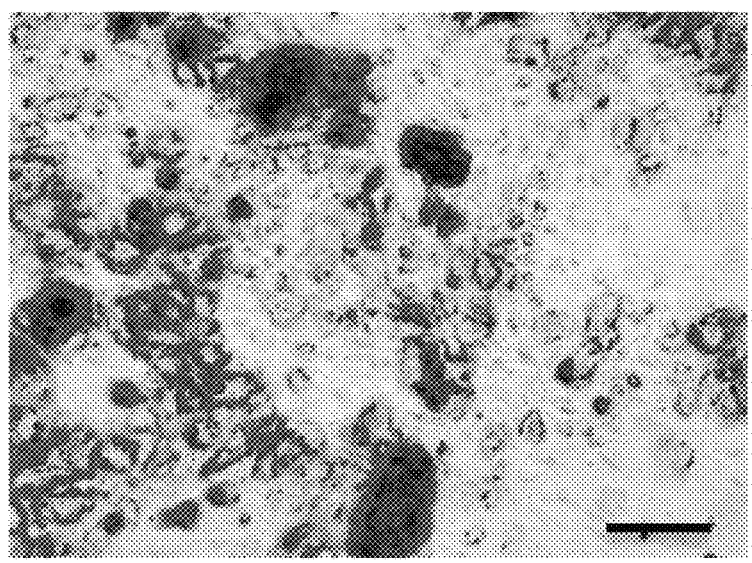
FIGS. 11A-E shows multipotency of discogenic cells.
Figure 11B:
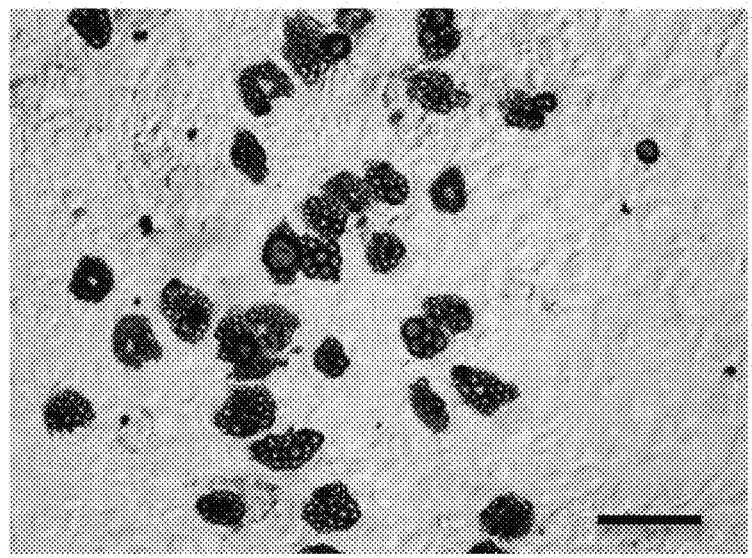
Figure 11C:
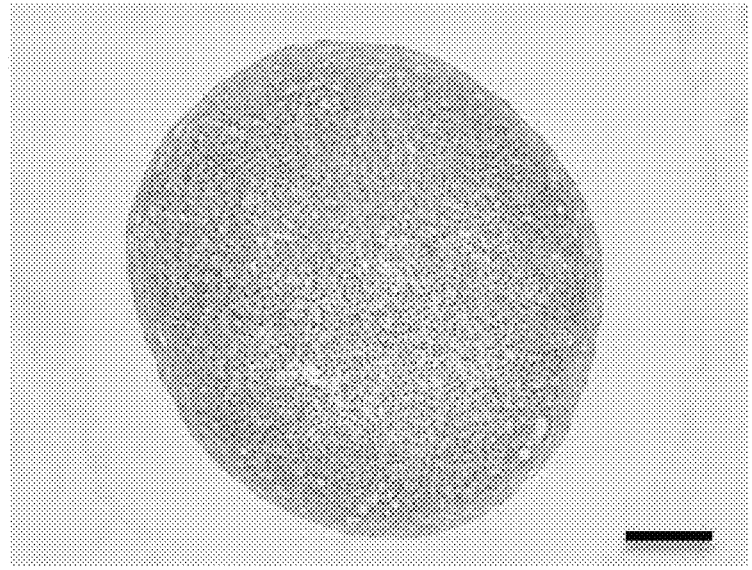

The discogenic cells were tested for their ability to form bone, fat and cartilage according to standard differentiation protocols. Robust adipogenesis and osteogenesis was observed by staining monolayers of differentiated cells (FIG. 11A-B). Discogenic cells formed large, hard micromasses of cartilage upon differentiation that stained positively for proteoglycan (FIG. 11C).

Figure 11D:
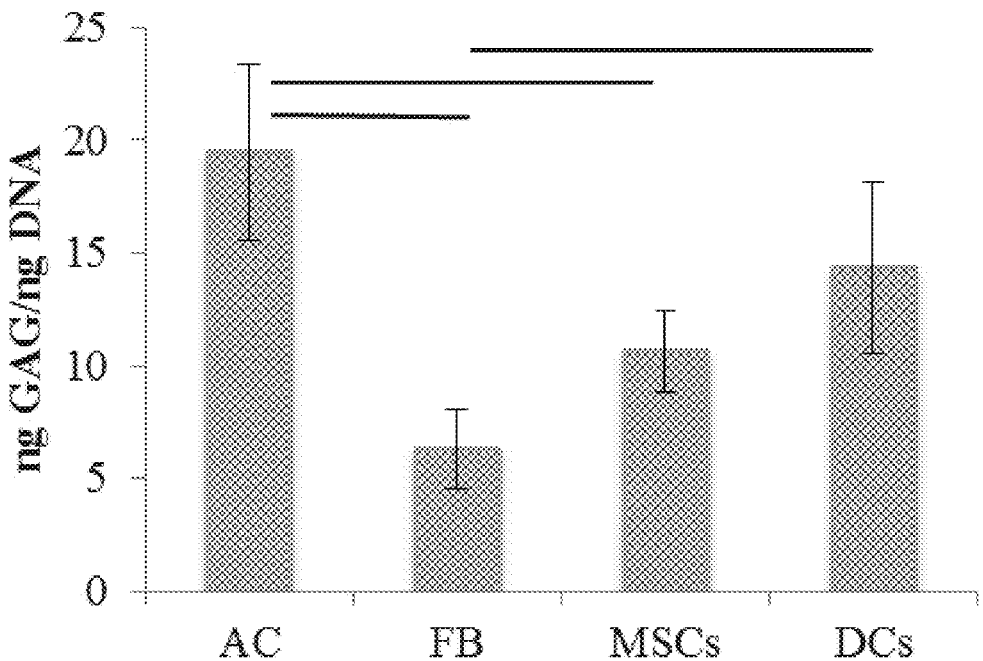
Figure 11E:
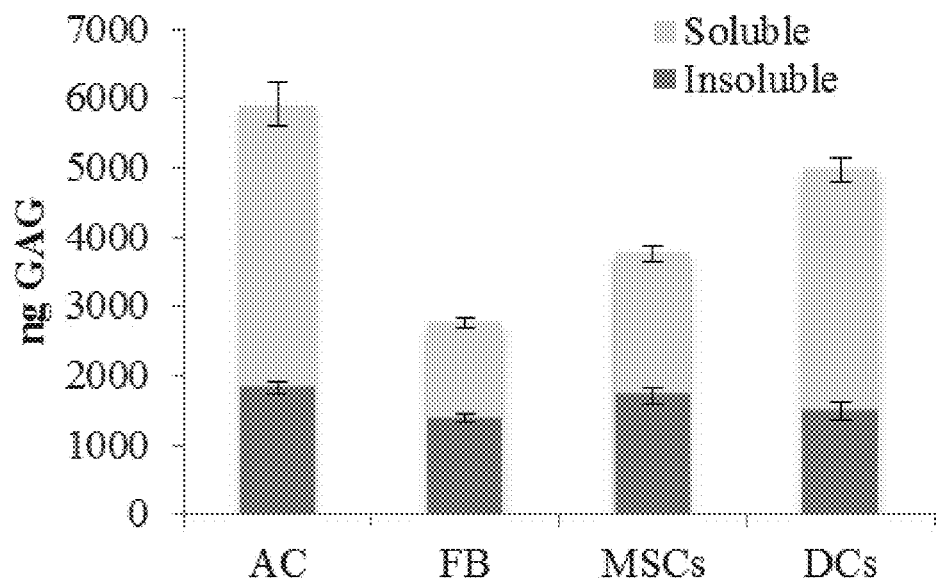

After 3 weeks in culture, the media and micromasses were assayed quantitatively for proteoglycan content. Discogenic cells (DCs) were compared to articular chondrocytes (AC), fibroblasts (FB) and mesenchymal stem cells (MSCs). As depicted in FIG. 11E, while the insoluble (micromass) quantity of proteoglycan did not change significantly by cell type, the amount of soluble proteoglycan measured varied considerably. When these two sources of matrix were combined and normalized to DNA content (FIG. 11D), discogenic cells where shown to produce more proteoglycan/DNA than fibroblasts (p<0.01), comparable levels to MSCs and articular chondrocytes.

Example 9

In Vivo Pilot Study in Rabbits

Female New Zealand White rabbits (3-4 kg) were used for these studies, under approval by private IACUC. Three rabbits were fasted overnight prior to surgery. For the first surgery to induce degeneration, animals were anesthetized intravenously and the surgical site prepared for aseptic surgery. An 8-10 cm longitudinal incision was made on the left lateral abdomen between the iliac crest and the last rib. The lumbar vertebral discs were accessed via retroperitoneal approach using blunt dissection. An 18 gauge needle was then inserted at least 5 mm into the lumbar vertebral discs of interest to create disk injury. Discs L2-L3, L3-L4, L4-L5, L5-L6 were injured using this technique. L5-L6 was left undisturbed. Muscle and skin were then closed in two or three layers using sutures, and the animals monitored during recovery. Prior to this study, 6 rabbits were injured and assessed for 8 weeks to confirm the creation of a stable and appropriate defect (data not shown).

After 2 weeks, the rabbits were again prepared for surgery and anesthetized, and the discs accessed as previously described. A 27-gauge needle was used to injected 25 ul of either the cell therapy containing 30,000 cells (L5-L6) or scaffold alone (L4-L5). For high dose therapy, 300,000 cells were injected. One disc was not modified to serve as injured control (L2-L3). The injection was held in place for 5 seconds, and when the needle was removed no material was observed to leak out.

For 6 weeks, animals were monitored for any adverse events or health concerns. Body weight was measured every week. Additionally, x-rays of the lumbar spine were performed every 2 weeks by anesthetizing the animal briefly (FIG. 12A). The distances between boney landmarks (three measurements of the disc space, 3 measurements of the left-adjacent vertebral bone) were measured on plain radiographs using a micrometer by a single individual and normalized against week 0 distances to assess Disc Height Index (DHI) percent.

After 6 weeks, the rabbits were euthanized; the discs were harvested and prepared for histology using paraffin. Sections (4 µm) were stained with a mixture of hematoxylin and eosin, or Alcian blue and eosin.

Statistical Analysis

All statistical analyses were performed using StatPlus software (AnalystSoft; Vancouver, Canada) utilizing Tukey's post-hoc tests. The p-values for significance were indicated in each study. A one-way analysis of variance (ANOVA) was used to compare the surface marker expression and proteoglycan production of discogenic cells in vitro. A two-way ANOVA was used to analyze the disc height data over time, and a one-way ANOVA was utilized for comparing histological scores at week 6. Graphs show mean with error bars representing standard deviation of the data set.

Results

As described above, surgical puncture was used to induce 'degeneration' in the intervertebral discs of 3 New Zealand White rabbits (n=3 condition). At the time of injury, nucleus pulposus material was noted to extrude from the needle track after the needle was removed. After surgery, animals did not show any unusual signs of distress due to the injury. After 2 weeks, an injection of low dose, high dose, or scaffold control was administered to the discs, with pressure held for 5 seconds before removing the needle. After injection, some material was noted to extrude out of the disc after the needle was removed.

Over the 6 week course of the study, no safety issues were noted. No major changes in body weight were observed after initial injury (FIG. 12B; 3.4 grams pre-injury to 3.3 grams at day 7, on average) or after cell therapy injection (FIG. 12B; 3.2 grams on average). No health or behavioral issues were reported by the animal care staff regarding any of the animals after receiving injections of the human cells into their discs.

Notable changes in disc height were measured over the course of 6 weeks by x-ray (a representative x-ray is at FIG. 12A, which also shows measurement methods). Two weeks after injury, all discs decreased to 59% of the original height on average. At week 4 and 6, the discs treated with low dose and high dose showed significant improvements in disc height compared to both scaffold and injured controls, from 70% and 64% DHI to 94% and 71% DHI, respectively (p<0.001) (FIG. 12C). Injection of the scaffold control was slightly better than no injection at all, represented by the injured control (64% DHI and 53% DHI, respectively; p<0.01).

Histologically, H&E images revealed normalization of disc architecture with cell therapy treatment. The height of the nucleus pulposus, from end-plate to end-plate, decreased with injury and increased with cell therapy (FIG. 13A). As shown in FIG. 13B, no immune reaction or abnormal tissue formation was noted in bone marrow, annulus fibrosus (AF), cartilage endplates (CEP) or nucleus pulposus (NP) after treatment. The nucleus pulposus remained dense with proteoglycan, as shown by alcian blue staining (FIG. 13B).

Example 10

In Vivo Pilot Study in Pigs

Female Gottingen minipigs (10-15 kg) were used for this research, under approval by private IACUC. Two pigs were fasted overnight prior to surgery. The injury surgery was performed as described above in Example 9, with addition of fluoroscopic imaging to confirm proper placement of needles, injuring discs L2-L3, L3-L4 and L3-L4. L5-L6 was left undisturbed. Muscle and skin were then closed in two or three layers using sutures, and the animals monitored during recovery. Prior to this study, 6 minipigs were injured and assessed for 12 weeks to confirm the creation of a stable and appropriate defect (data not shown).

After 2 weeks, the pigs were again prepared for surgery and anesthetized, and the discs accessed as previously described. A 27-gauge needle was used to injected 150 ul of either the cell therapy containing 100,000 cells (High Dose; animal 1: L3-L4, L4-L5), 500,000 cells (Low Dose; animal 2: L3-L4, L4-L5) or scaffold alone (L2-L3). One disc was not modified to serve as injured control (L2-L3). The injection was held in place for 5 seconds, and when the needle was removed no material was observed to leak out.

For an additional 10 weeks, animal were monitored for any adverse events or health concerns. Body weight was measured every week. Additionally, x-rays of the lumbar spine were performed at 4, 8 and 12 weeks by anesthetizing the animal briefly, and DHI determined as described above. After 12 weeks, the pigs were euthanized; the discs were harvested and prepared for histology using paraffin as previously described.

Results

Figure 14A:
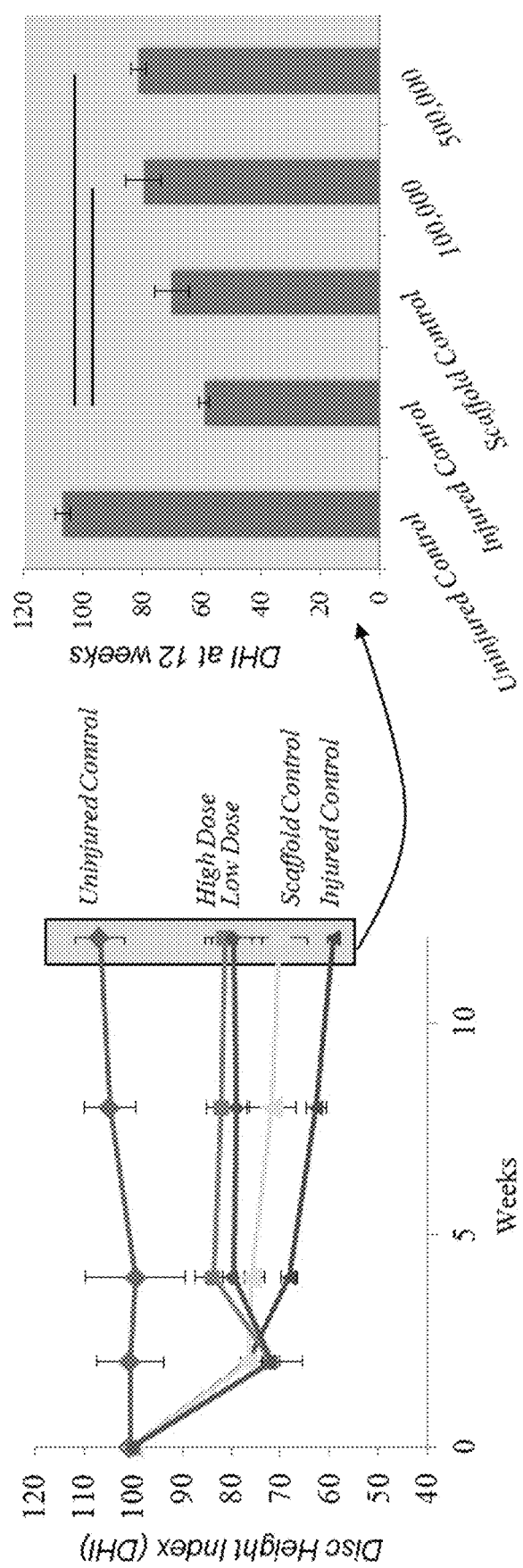

Injury of pig discs resulted in 20-30% reduction in disc height. Upon treatment, both the low and high dose treatment resulted in immediate improvement in disc height that was sustained to week 12 and was better than the injured control (p<0.05). The scaffold and injured control did not improve over time (FIG. 14A). Fluoroscopic imaging was used to aid in correct needle placement, and shows the differences in disc height along an injured spine (FIG. 14B). Similar to the rabbit pilot study described above, no immune reaction or abnormal tissue formation was noted in nucleus pulposus, cartilage endplate, annulus fibrosus or bone marrow (not shown), with the nucleus pulposus staining for proteoglycan similarly to untreated tissue (FIG. 14C).

It is noted that there are alternative ways of implementing the embodiments disclosed herein. While a number of exemplary aspects and embodiments have been discussed above, those of skill in the art will recognize certain modifications, permutations, additions and sub combinations thereof. Accordingly, the present embodiments are to be considered as illustrative and not restrictive. Furthermore, the claims are not to be limited to the details given herein, and are entitled their full scope and equivalents thereof.

What is claimed is:

1. A discogenic cell population comprising:
   cells derived from mammalian nucleus pulposus disc tissue, wherein the cell population has been passaged at least one time in an anchorage dependent culture, and transferred and maintained in-vitro in anchorage independent culture comprising methylcellulose at a concentration of about 0.1% to about 5% or a low adhesion coating, wherein the cell population, after seven days in anchorage independent culture, expresses at least 2-fold more aggrecan gene and collagen 2 gene than a population of nucleus pulposus cells derived from mammalian disc tissue grown in anchorage dependent culture, and wherein less than about 40% of the cell population expresses the cell surface markers CD24 and CD105.

2. The cell population of claim 1, where the anchorage independent culture comprises a media comprising one or more additives selected from EGF, bFGF, and serum, and wherein the methylcellulose has a concentration of about 0.6% to about 0.9%.

3. The cell population of claim 2, wherein the cell population is passaged in a culture receptacle comprising a low adhesion coating.

4. The cell population of claim 3, wherein expression of the aggrecan gene and collagen 2 gene is at least 5-fold greater than the same genes expressed in a population of nucleus pulposus cells derived from mammalian disc tissue grown in anchorage dependent culture.

5. The cell population of claim 4, wherein the population further produces one or more cell surface markers selected from the group comprising CD34, CD44, CD73, CD90, CD166, Stro-1, HIF1, nestin, CK8, and HLA proteins.

6. The cell population of claim 5, wherein the percentage of the cells producing the one or more cell surface markers of claim 5 is greater than 70% or less than 40%.

7. The cell population of claim 1, wherein the population expresses one or more genes or gene products selected from the group comprising GAPDH, SDHA, HPRT1, B2M, Sox9, Col1, nestin, CK8, Sox1, CD44, ALPI, and PPARG.

8. The cell population of claim 1, wherein the cell population is obtained from human intervertebral disc tissue.

9. A method of using the discogenic cell population of claim 1 to treat at least one disc in a subject in need thereof comprising:
    administering a therapeutic amount of the discogenic cell population of claim 1 to the subject, thereby treating the subject.

10. A method of treating a subject having at least one diseased or damaged intervertebral disc, comprising:
    administering to the subject the discogenic cell population of claim 1, in an amount effective to treat the disease or damage.

11. A method of treating an indication selected from the group consisting of degenerative disc disease, herniated disc, and injured disc, comprising:
    administering a therapeutic amount of the discogenic cell population of claim 1, thereby treating the indication.

12. A method of deriving the discogenic cell population of claim 1 comprising:
    isolating one or more cells from tissue;
    passaging the one or more cells in an anchorage dependent culture media;
    transferring the one or more cells to an anchorage independent culture media.

13. The method of claim 12, wherein the tissue is mammalian disc tissue.

14. The method of claim 13, wherein the tissue is donated organ tissue.

15. The method of claim 14, wherein the cell population is passaged at least one time in the anchorage independent culture media.

16. The method of claim 15, wherein the cell population produces extracellular matrix comprising aggrecan or a collagen.

17. The method of claim 16, wherein the cell population produces one or more cell surface markers selected from the group comprising CD24, CD34, CD44, CD73, CD90, CD105, CD166, Stro-1, HIF 1, nestin, CK8, and HLA proteins.

18. The method of claim 17, wherein the percentage of the cells in the population producing the one or more cell surface markers is greater than 70% or less than 40%.

19. The method of claim 12, wherein the cell population expresses one or more gene or gene products selected from the group comprising GAPDH, SDHA, HPRT1, B2M, Sox9, Aggrecan, Col1, Col2, nestin, CK8, Sox1, CD44, ALPI, PPARG, ADAMTS, MMP, FMOD, and IL.

20. A device for treating a diseased or injured intervertebral disc comprising:
    the discogenic cell population of claim 1, wherein at least one cell has been grown in anchorage independent culture; and
    a scaffold, matrix, or implantable structure.

21. The device of claim 20, wherein the device further comprises a biological active agent.

22. An artificial disc replacement device comprising:
    an artificial outer annulus, wherein the outer annulus is comprised of a resorbable or non-resorbable material; and
    the discogenic cell population of claim 1.

23. The artificial disc replacement device of claim 22, wherein the outer annulus is comprised of a non-resorbable material.

24. The artificial disc replacement device of claim 23, wherein the non-resorbable material is polyurethane.

25. The artificial disc replacement device of claim 22, wherein the outer annulus is comprised of a resorbable material.

26. The artificial disc replacement device of claim 25, wherein the resorbable material is polygycolic acid or polylactic acid, or a combination thereof.

27. The artificial disc replacement device of claim 22, wherein the discogenic cell population further comprises one or more of the following: a scaffold material, a matrix material, a carrier material, a growth factor(s), or other biologically active agents.

28. The artificial disc replacement device of claim 22, further comprising an attachment means for fixedly securing the device to one or more vertebral bodies.

29. The artificial disc replacement device of claim 28, further comprising through-holes, cuffs, tabs, loops, or washers to allow for screw fixation to one or more vertebral bodies.

30. A method of replacing a spinal disc comprising:
    producing the artificial disc of claim 22 in vitro; and
    surgically implanting the artificial disc into a subject, thereby replacing the spinal disc.

* * * * *